(12) United States Patent
Matsui et al.

(10) Patent No.: US 7,943,816 B2
(45) Date of Patent: May 17, 2011

(54) ARACHIDONIC ACID-CONTAINING PLANTS AND USE OF THE PLANTS

(75) Inventors: Keisuke Matsui, Osaka (JP); Ren Chen, Fukuoka (JP)

(73) Assignee: Suntory Holdings Limited, Osaka-shi (JP)

( * ) Notice: Subject to any disclaimer, the term of this patent is extended or adjusted under 35 U.S.C. 154(b) by 936 days.

(21) Appl. No.: 10/583,084

(22) PCT Filed: Dec. 14, 2004

(86) PCT No.: PCT/JP2004/018638
§ 371 (c)(1),
(2), (4) Date: May 25, 2007

(87) PCT Pub. No.: WO2005/059130
PCT Pub. Date: Jun. 30, 2005

(65) Prior Publication Data
US 2008/0052795 A1    Feb. 28, 2008

(30) Foreign Application Priority Data

Dec. 17, 2003   (JP) ................................ 2003-419124
Mar. 29, 2004   (JP) ................................ 2004-097089

(51) Int. Cl.
C12N 5/04       (2006.01)
C12N 5/10       (2006.01)
C12N 15/82      (2006.01)
A01H 5/00       (2006.01)
C07H 21/04      (2006.01)

(52) U.S. Cl. ........ 800/278; 800/281; 800/288; 800/312; 435/410; 435/415; 435/468; 435/320.1; 536/23.74

(58) Field of Classification Search .......................... None
See application file for complete search history.

(56) References Cited

U.S. PATENT DOCUMENTS

| | | | | |
|---|---|---|---|---|
| 5,968,809 A * | 10/1999 | Knutzon et al. | ............ | 435/254.2 |
| 6,459,018 B1 | 10/2002 | Knutzon | | |
| 6,677,145 B2 * | 1/2004 | Mukerji et al. | ................ | 435/193 |
| 6,913,916 B1 * | 7/2005 | Mukerji et al. | ................ | 435/183 |
| 7,179,647 B2 * | 2/2007 | Lerchl et al. | .................. | 435/325 |

FOREIGN PATENT DOCUMENTS

| | | | |
|---|---|---|---|
| JP | 2001-527395 | | 12/2001 |
| JP | 2002-517255 | | 6/2002 |
| WO | WO 99/64616 | * | 12/1999 |
| WO | WO 00/52183 | | 9/2000 |
| WO | WO 03/093482 A2 | | 11/2003 |
| WO | WO 2004/057001 | | 7/2004 |
| WO | WO 2004/071467 A2 | | 8/2004 |

OTHER PUBLICATIONS

Drexler et al., "Metabolic engineering of fatty acids for breeding of new oilseed crops: strategies, problems and first results," *J. Plant Physiol.*, vol. 160, pp. 779-802 (2003).

Search Report dated Jan. 19, 2007 from European Patent Appln. No. 04806999.1.
Toshihiko Niina et al., "Plant Metabolic Engineering", NTS Inc, pp. 574-586, Jun. 25, 2002, [ Japanese language and partial translation].
Yoshikazu Tanaka, "Production of Polyunsaturated Fatty Acids in Soybeans", Material of $8^{th}$ workshop in $160^{th}$ committee on Biotechnology for Global Environment, Foods and Resources, Japan Society for the Promotion of Science, pp. 14-16, Jun. 13, 2003 [ Japanese language and partial translation].
Yoshikazu Tanaka et al., "Research and Development of Polyunsaturated Fatty Acid-Producing Soybeans", Suntory Limited, A Report on the Results of Research and Development on Biomass Energy Utilization Rationalization Industrial Technology, pp. 1-16, Nov. 5, 2002.
Yoshifumi Shinmen et al., "Production of Arachidonic Acid by *Mortierella* Fungi", Applied Microbiology Biotechnology, vol. 31, pp. 11-16, 1989.
DS Knutzon et al., "Modification of Brassica Seed Oil by Antisense Expression of a Stearoyl-Acyl Carrier Protein Desaturase Gene", PNAS, vol. 89, pp. 2624-2628, Apr. 1992.
Olga Sayanova et al., "Expression of Borage Desaturase cDNA containing an N-terminal cytochrome b5 domain results in the accumulation of high levels of Delta 6-desaturated fatty acids in transgenic tobacco", PNAS, vol. 94, pp. 4211-4216, Apr. 1997.
Hjördis Drexler et al., "Metabolic Engineering of Fatty Acids for breeding of new oilseed crops: strategies, problems and first results", Journal of Plant Physiology, vol. 160, pp. 779-802, 2003.
Ian E. Burbulis et al., "Interactions Among Enzyme of the Arabidopsis flavonoid biosynthetic pathway", PNAS, vol. 96, No. 22, pp. 12929-12934, Oct. 26, 1999.
Jitao Zou et al., "Modification of Seed Oil Content and Acyl Composition in the Brassicaceae by Expression of a Yeast sn-2 Acyltransferase Gene", The Plant Cell, vol. 9, pp. 909-923, Jun. 1997.
Toni A. Voelker et al., "Fatty Acid Biosynthesis Redirected to Medium Chains in Transgenic Oilseed Plants", Science, vol. 257, pp. 72-74, Jul. 3, 1992.
Michael G. Koziel et al., "Field Performance of Elite Transgenic Maize Plants Expressing an Insecticidal Protein Derived from *Bacillus thuringiensis*", Bio/Technology, vol. 11, pp. 194-200, Feb. 1993.
Eliane R. Santarém et al., "Transformation of Soybean [*Glycine max* (L.) Merrill] Using Proliferative Embryogenic Tissue Maintained on Semi-Solid Medium", In Vitro Cell. Dev. Biol.-Plant, vol. 35, pp. 451-455, Nov.-Dec. 1999.
Search Report from International PCT Application No. PCT/JP2004/018638 mailed Feb. 1, 2005.

(Continued)

*Primary Examiner* — Eileen B O Hara
(74) *Attorney, Agent, or Firm* — Drinker Biddle & Reath LLP

(57) ABSTRACT

The present invention provides arachidonic acid-containing plants and soybeans, and a method of use thereof. The arachidonic acid-containing plant is produced by a process that includes an arachidonic acid producing step in which fatty acid synthetase genes associated with the biosynthesis of arachidonic acid are introduced into a plant to produce arachidonic acid. Thus, plants or soybeans containing arachidonic acid can easily be obtained. Therefore, it is possible to obtain a large amount of arachidonic acid at low cost.

11 Claims, 3 Drawing Sheets

OTHER PUBLICATIONS

Napier et al., "Towards the production of pharmaceutical fatty acids in transgenic plants," Journal of the Science of Food and Agriculture, 81:883-888, 2001.

Domergue et al., "Acyl Carriers Used as Substrates by the Desaturases and Elongases Involved in Very Long-chain Polyunsaturated Fatty Acids Biosynthesis Reconstituted in Yeast," The Journal of Biological Chemistry, vol. 278, No. 37, Issue of Sep. 12, pp. 35115-35126, 2003.

Official Action issued Jul. 18, 2008 in EP application No. 04 806 999.1.

Lin et al., "Efficient linking and transfer of multiple genes by a multigene assembly and transformation vector system," *PNAS*, May 13, 2003, vol. 100, No. 10, pp. 5962-5967.

Goderis et al., "A set of modular plant transformation vectors allowing flexible insertion of up to six expression units," *Plant Molecular Biology*, vol. 50, 2002, pp. 17-27.

Matsui et al., "Research and Development of Highly Polyunsaturated Fatty Acid Producing Soybean seeds," *Research Association for Biotechnology*, pp. 2-6 (Published Nov. 11, 2003) (in Japanese w/English translation).

Chen et al., "Functional analysis of regulatory elements in a plant embryo-specific gene," *Proc. Natl. Acad. Sci. USA*, vol. 83, pp. 8560-8564 (Nov. 1986).

\* cited by examiner

ARACHIDONIC ACID-CONTAINING PLANTS AND USE OF THE PLANTS

CROSS REFERENCE TO RELATED APPLICATIONS

This application is a National Stage of International Application No. PCT/JP2004/018638, filed Dec. 14, 2004, which claims the benefit of Japanese Patent Application No. 419124/2003, filed on Dec. 17, 2003 and Japanese Patent Application No. 97089/2004, filed on Mar. 29, 2004, and are incorporated by reference herein in their entirety.

TECHNICAL FIELD

The present invention relates to arachidonic acid-containing plants (e.g. soybean (*Glycine max*)) and use of the plants, and particularly, relates to (i) plants obtained by a producing process of arachidonic acid-containing plants by introducing a gene of an enzyme involved in arachidonic acid synthesis, and (ii) use of the plants.

BACKGROUND ART

Fatty acids are main constituents of lipids, which are one of the three major nutrients for living organisms, and often refer to aliphatic monocarboxylic acids which are derived from natural lipids by hydrolysis. Generally, aliphatic chains of which are saturated are referred to as saturated fatty acids, and aliphatic chains of which contain a double bond or triple bond are referred to as unsaturated fatty acids. Fatty acids are classified into short-chain fatty acids (2 to 4 carbon atoms), medium-chain fatty acids (5 to 14 carbon atoms), long-chain fatty acids (16 to 18 carbon atoms), and very long-chain fatty acids (20 or more carbon atoms). When the number of carbon atoms is n and the number of double bonds is m, the fatty acids are often denoted by Cn:m.

The fatty acids are also the main constituents of the cell membrane of plants, and are important components accumulated predominantly in the form of triglycerides to provide energy sources in seeds and fruits. The amount of lipids accumulated in plants, and their fatty acid composition differ depending upon the types of plants. Examples of main fatty acids accumulated in plants include: palmitinic acid (C16:0) that is a saturated fatty acid with 16 carbon atoms (C16); and stearic acid (C18:0) that is a saturated fatty acid with 18 carbon atoms (C18). Other examples include unsaturated fatty acids with 18 carbon atoms (C18) having unsaturated bonds, such as oleic acid (C18:1) having one double bond, linoleic acid (C18:2) having two double bonds, and α-linolenic acid (C18:3α) having three double bonds. Plants containing a relatively large amount of these fatty acids, such as soybean, oil palm, sunflower, rapeseed, and coconut palm, are cultivated as fat or oil source plants (also referred to as oil plants). Note that, fatty acids having 18 or more carbon atoms and two or more unsaturated bonds (double bonds or triple bonds) are collectively referred to as Poly Unsaturated Fatty Acid (PUFA).

Incidentally, higher animals generally do not have desaturases involved in the syntheses of linoleic acid and α-linolenic acid, and therefore need intake of the PUFAs from plants (foods from vegetable sources). Therefore, linoleic acid and α-linolenic acid are referred to as essential fatty acids. In the body of higher animals, desaturation and elongation of carbon chains are repeated using these unsaturated fatty acids as substrates, so as to synthesize various unsaturated fatty acids, including dihomo-γ-linolenic acid, arachidonic acid (C20: 4n-6), eicosapentaenoic acid (EPA) (C20:5n-3), and docosahexaenoic acid (DHA) (C22:6n-3).

It is known that these PUFAs have various functions for the metabolism in the body of higher animals, and play an important role as direct precursors of prostaglandins. Particularly, elderly people and infants, who have a reduced biosynthesis ability for dihomo-γ-linolenic acid, arachidonic acid, EPA, DHA, and fatty acids need intake of these fatty acids from foods. Particularly, arachidonic acid is known to be effective in improving senile dementia. Therefore, health foods mainly composed of arachidonic acid have been commercially available, and there has been an increasing demand for arachidonic acid.

Fish oil has a relatively high content of arachidonic acid, and arachidonic acid is now supplied in part by extraction from fish oil. However, in view of the problems such as depletion of fish, instable supply, and contamination of oil or fat resources caused by environmental pollution, arachidonic acid has been recently produced by microbial fermentation using microorganisms such as *Mortierella*, which is superior in terms of control of productivity, stability of long-term supply, cleanliness, and relative ease of purification, for example (e.g. see Document 1: Appl. Microbiol. Biotechnol., 31, p 11 (1987)). However, the microbial fermentation currently raises problems in that it requires a high production cost and a capital investment for scale-up, which cannot be carried out easily.

Therefore, if these PUFAs, particularly arachidonic acid, can be produced in oil plants, a significant improvement in the efficiency of their production can be expected, as well as cost reduction. In recent years, PUFA production in higher plants has been suggested by isolating desaturase genes and chain elongase genes, essential for the PUFA biosynthesis, from plants, animals, fungi, and yeasts, and by introducing these genes into higher plants.

Examples of plants whose oil or fat compositions are actually modified by genetic recombination include: (i) lauric acid-producing rapeseed (transgenic rapeseed obtained by isolating a medium-chain acyl-ACP thioesterase gene from laurel, which contains a relatively large amount of lauric acid, and then by introducing the gene, which specifically acts on C12:0-ACP (Acyl Carrier Protein) and releases lauric acid, into rapeseed by ligating it to the promoter of a napin gene that encodes a storage protein of the rapeseed; see Document 2: Science, 257, p 72 (1992)); (ii) high stearic acid content rapeseeds (recombinant rapeseeds with an increased stearic acid content as high as 40%, produced by introducing an antisense gene to suppress expression of a C18:0-ACP desaturase gene; see Document 3: Proc. Natl. Acad. Sci. U.S.A., 89, p 2624 (1992)); (iii) high erucic acid (C22:1) content rapeseeds (rapeseeds containing as high as 90% erucic acid, produced by introducing an LPAAT gene of yeast; see document 4: Plant Cell, 9, p 909 (1997)); (iv) high oleic acid content soybeans (soybeans with an increased oleic acid content as high as 80% compared with the original level of about 23%, produced by suppressing the expression of Δ12 desaturase gene Fad2 in soybean seeds and thereby suppressing the synthetic pathway producing linoleic acid from oleic acid, wherein a promoter derived from the β-conglycinin gene encoding a soybean seed storage protein was used as the Fad2-controlling promoter); and (v) γ-linolenic acid producing rapeseeds (rapeseeds produced by introducing Δ6 desaturase gene isolated from *Borago officinalis*; see Document 5: Proc. Natl. Acad. Sci. U.S.A., 94, p 4211 (1997)). Further, it has been reported that arachidonic acid and EPA were produced in flax plants by expressing Bacillariophyceae-derived Δ6 desaturase gene and Δ5 desaturase gene and a *physcomi-*

*trella patens*—derived chain elongase gene (see Document 6: J. Biol. Chem. 278, p 35115, (2003)).

Further, for the production of soybeans producing polyunsaturated fatty acids, gene introduction has been attempted by isolating the cDNAs of Δ6 desaturase, chain elongase, and Δ5 desaturase from *Mortierella*, which produces polyunsaturated fatty acids, and by ligating these cDNAs to various promoters (e.g. see document 11: "*Shokubutu Riyou Enerugi Shiyou Gourika Seisan Gijutsu no Kenkyu Kaihatu Seika Houkokusho*" (report on the results of research and development on biomass energy utilization rationalization industrial technology) reported in 2002; and document 12: Yoshikazu Tanaka, "*Chikyu Shokuryou Shigen no tame no Shokubutu Baio Dai* 160 *Iinkai Dai* 8 *Kenkyukai Shiryou*" (Material of 8th workshop in 160th Committee on biotechnology for global environment, foods, and resources), (Japan Society for the promotion of science), p 14-16, held on Jun. 13, 2003). Note that, the descriptions herein are based on Document 7: "Plant metabolic engineering", NTS Inc., ISBN4-86043-004-2C3045, p 574-586 (2002), or document 8: J. Plant Physiol. 160, p 779 (2003), unless otherwise noted.

However, the description in Document 6 reporting on arachidonic acid-producing plants remains unclear and its disclosure is insufficient.

More specifically, for the introduction of foreign genes into plants to modify the composition or quality of oil or fat in the plants, it is necessary to control the expression of a gene of an enzyme involved in the determination of carbon-chain length, or a gene for a desaturase that determines the number and position of double bond. Further, for the production of fatty acids which are not inherent to the host plant, the time and site of fatty acid synthesis, and the form of the fatty acids in the cells must be considered to prevent adverse effects of the fatty acids on the growth of the host plant.

Still further, in the expression of genes of foreign organisms, particularly non-plants, there are cases where the transcripts are processed. In such a case, for example, codon modification or other process must be carried out (e.g. see document 9: Bio/Technology 11 p 194, 1993).

Further, enzymes involved in a series of biosynthesis reactions forms a complex in the cell, and metabolites of these enzymes may be metabolized through the molecular channel (e.g. document 10: Proc. Natl. Acad. Sci. U.S.A. 96, p 12929 (1999)). In such a case, even if a gene of an enzyme involved in the biosynthesis is known and its gene introduction technique is known, it is very difficult to predict how the enzyme produced by the introduced foreign gene functions and produces a desired substance in the host plant.

In this regard, Document 6 is insufficient because it is totally silent about such problems. As described above, the biosynthesis of fatty acid is unclear largely. Specifically, it is not clear as to whether (i) transcription and translation of fatty acid synthesizing genes derived from foreign organisms, e.g. *Mortierella* are carried out efficiently in plants, (ii) whether enzymes encoded by these genes can function well in plants, (iii) whether the enzymes can function cooperatively with a group of lipid synthetases in the cells of plants, or (iv) whether the arachidonic acid can accumulate in the form of triglycerides to provide an oil body as do other fatty acids, for example. That is, the production of arachidonic acid by the introduction of a foreign gene into plants takes tedious trial and error.

Further, as to legume plants, particularly soybeans, difficulties of genetic transformation by gene introduction have been pointed out, and there is scant information regarding transformation of soybeans. According to some reports, transformation efficiencies and regeneration efficiencies of soybeans are extremely low, and only some species of soybeans can be transformed (e.g. see Document 13: Santarem E R and Finer J J (1999), In Vitro Cell. Dev. Biol. Plant 35, p 451-455). Therefore, (i) it is necessary to develop a transformation system for soybeans, which do not easily accept foreign genes, and (ii) it is necessary to develop a stable multi-gene expression system which stably expresses multiple genes required for the synthesis of polyunsaturated fatty acids. In addition, (iii) it is necessary to confirm whether or not gene products derived from foreign organisms (enzymes involved in fatty acids synthesis) are actually expressed in the soybeans at a protein level and have an enzymatic activity, that is, whether or not lipid compositions of the transformed soybeans were altered.

Thus, the production of polyunsaturated fatty acids in soybeans is an extremely difficult technique and requires a multistage technological development. In fact, in the reports of Documents 11 and 12, transformant soybeans (plants) which produce polyunsaturated fatty acids are not obtained.

Further, in Documents 6, 11, and 12, there is no report on transformant plants whose trait of producing polyunsaturated fatty acids (e.g. arachidonic acid) is inherited to the next generation. That is, transformation of plants for the production of polyunsaturated fatty acids itself is attended with much technical difficulty. Therefore, it is much more difficult to obtain subsequent generations of plants that inherit the trait of producing polyunsaturated fatty acids.

Therefore, there is a strong demand for solving the foregoing problems and thereby realize, through trial and error, arachidonic acid-containing plants, particularly arachidonic acid-containing soybeans, which are produced by actually introducing a gene derived from foreign organisms into plants and then confirming not only its expression in a DNA level but also the expression of an enzyme in a protein level, followed by confirmation of the enzyme function. Further, it has been strongly demanded to obtain transformant plants that inherit the trait of producing polyunsaturated fatty acids to the next generation.

DISCLOSURE OF INVENTION

The present invention was made in view of the foregoing problems, and an object of the invention is to provide arachidonic acid-containing plants and a method of use thereof.

In accomplishing the present invention, the inventors prepared a recombinant expression vector in which three kinds of *Mortierella*-derived genes for Δ6 desaturase, fatty-acid-chain elongase, and Δ5 desaturase were ligated downstream of a soybean seed-specific promoter with a terminator. The recombinant expression vector was introduced into a soybean embryo to prepare a transformed soybean. As a result, the inventors have found, for the first time, that the foreign genes were actually expressed in the soybean at a protein level, and that the proteins were actually functional as enzymes to produce arachidonic acid. It was also confirmed that the transformed soybean actually contained arachidonic acid.

In order to solve the foregoing problems, an arachidonic acid-containing plant according to the present invention is produced by a process that includes an arachidonic acid producing step in which fatty acid synthetase genes associated with the biosynthesis of arachidonic acid are introduced into a plant to produce arachidonic acid.

It is preferable that the arachidonic acid producing step include a transforming step in which a recombinant expression vector containing genes encoding the fatty acid synthetases associated with the biosynthesis of arachidonic acid are introduced into a plant cell.

It is preferable that the arachidonic acid producing step further include a recombinant expression vector constructing step of constructing a recombinant expression vector.

It is preferable that the recombinant expression vector constructing step include a step in which the genes encoding the fatty acid synthetases associated with the biosynthesis of arachidonic acid are ligated downstream of a soybean seed-specific promoter.

It is preferable that the fatty acid synthetases associated with the biosynthesis of arachidonic acid be Δ6 desaturase, a fatty-acid-chain elongase, and a Δ5 desaturase.

It is preferable that the Δ6 desaturase be one of: (a) a protein consisting of an amino acid sequence of SEQ ID NO: 1; and (b) a protein, consisting of an amino acid sequence that has been modified by substitution, deletion, insertion, and/or addition of one or more amino acids of SEQ ID NO: 1, for catalyzing a reaction of introducing an unsaturated bond at position Δ6 of an aliphatic monocarboxyl acid.

It is preferable that the gene encoding the Δ6 desaturase be one of: (c) a gene having a base sequence of SEQ ID NO: 2 as an open reading frame; and (d) a gene that hybridizes under stringent conditions with a gene of a base sequence complementary to a base sequence of a gene identified by SEQ ID NO: 2, and that encodes a protein which catalyzes a reaction of introducing an unsaturated bond at position Δ6 of an aliphatic monocarboxyl acid.

It is preferable that the fatty-acid-chain elongase be one of: (e) a protein consisting of an amino acid sequence of SEQ ID NO: 3; and (f) a protein, consisting of an amino acid sequence that has been modified by substitution, deletion, insertion, and/or addition of one or more amino acids of SEQ ID NO: 3, for catalyzing a reaction of elongating a carbon chain of an aliphatic monocarboxyl acid.

It is preferable that the gene encoding the fatty-acid-chain elongase be one of: (g) a gene having a base sequence of SEQ ID NO: 4 as an open reading frame; and (h) a gene that hybridizes under stringent conditions with a gene of a base sequence complementary to a base sequence of a gene identified by SEQ ID NO: 4, and that encodes a protein which catalyzes a reaction of elongating a carbon chain an aliphatic monocarboxyl acid.

It is preferable that the Δ5 desaturase be one of: (i) a protein consisting of an amino acid sequence of SEQ ID NO: 5; and (j) a protein, consisting of an amino acid sequence that has been modified by substitution, deletion, insertion, and/or addition of one or more amino acids of SEQ ID NO: 5, for catalyzing a reaction of introducing an unsaturated bond at position Δ5 of an aliphatic monocarboxyl acid.

It is preferable that the gene encoding the Δ5 desaturase be one of: (k) a gene having a base sequence of SEQ ID NO: 6 as an open reading frame; and (l) a gene that hybridizes under stringent conditions with a gene of a base sequence complementary to a base sequence of a gene identified by SEQ ID NO: 6, and that encodes a protein which catalyzes a reaction of introducing an unsaturated bond at position Δ5 of an aliphatic monocarboxyl acid.

It is preferable that the fatty acid synthetases associated with the biosynthesis of arachidonic acid, or the genes encoding the fatty acid synthetases be derived from *Mortierella*. It is more preferable that the fatty acid synthetases associated with the biosynthesis of arachidonic acid, or the genes encoding the fatty acid synthetases be derived from *Mortierella alpina*.

It is preferable that the arachidonic acid producing step include an expression suppressing step of suppressing expression of a Δ15 desaturase in a host. It is preferable that, in the expression suppressing step, expression of the Δ15 desaturase be suppressed by an RNAi method.

The present invention includes plants containing the arachidonic acid produced by the foregoing oil or fat source plants. It is preferable that the plant be a plant cell, a plant tissue, a plant callus, a plant seed, a grown plant individual, or offspring of a plant individual having the same trait as the grown plant individual. It is more preferable that the plant be a soybean.

The present invention includes arachidonic acid obtained from the arachidonic acid-containing plant. The present invention also includes a composition which includes the arachidonic acid. Further, the invention includes food which includes the composition. The present invention also includes an arachidonic acid-containing plant preparation kit for preparing the arachidonic acid-containing plant, the arachidonic acid-containing plant preparation kit including at least a recombinant expression vector including a promoter and genes for encoding fatty acid synthetases associated with the biosynthesis of arachidonic acid. Preferably, the present invention includes a set of reagents for introducing the recombinant expression vector into a plant cell.

In order to achieve the invention, the inventors actually introduced a foreign gene into a plant, and, after trial and error, successfully produced oil or fat source plants, namely, soy beans, containing arachidonic acid. This is not hindsight based on prior art.

As described, the present invention provides arachidonic acid-containing plants produced by introducing into plants fatty acid synthetase genes associated with the biosynthesis of arachidonic acid, thereby enabling plants to produce arachidonic acid. The present invention is therefore effective in readily obtaining plants containing arachidonic acid. That is, the present invention enables arachidonic acid to be produced in plants. This is advantageous in terms of not only cost and, particularly, efficiency of the production but also mass production of arachidonic acid, as compared with obtaining arachidonic acid from fish oil or microorganisms.

Further, arachidonic acid-containing plants according to the present invention are highly effective in that their traits to produce polyunsaturated fatty acids are passed onto the next generation. Therefore, the characteristics of the modified fatty acids in the arachidonic acid-containing plants are passed onto the next generation plants. Thus, cultivating the arachidonic acid-containing plants enables the seeds of the arachidonic acid-containing plants to be mass produced with the modified fatty acid composition, thereby obtaining arachidonic acid in mass quantity over an extended time period.

The same effects can also be obtained in leguminous plants, for example, such as soybeans, which are relatively difficult to transform. That is, the present invention also includes arachidonic acid-containing soybeans, which can exhibit the same effects as the arachidonic acid-containing plants.

Arachidonic acid is an essential fatty acid in higher animals including humans. For this reason, arachidonic acid has been widely used in health food or medicines. The present invention can meet these increasing demands for arachidonic acid.

BEST MODE FOR CARRYING OUT THE INVENTION

Figure 1:
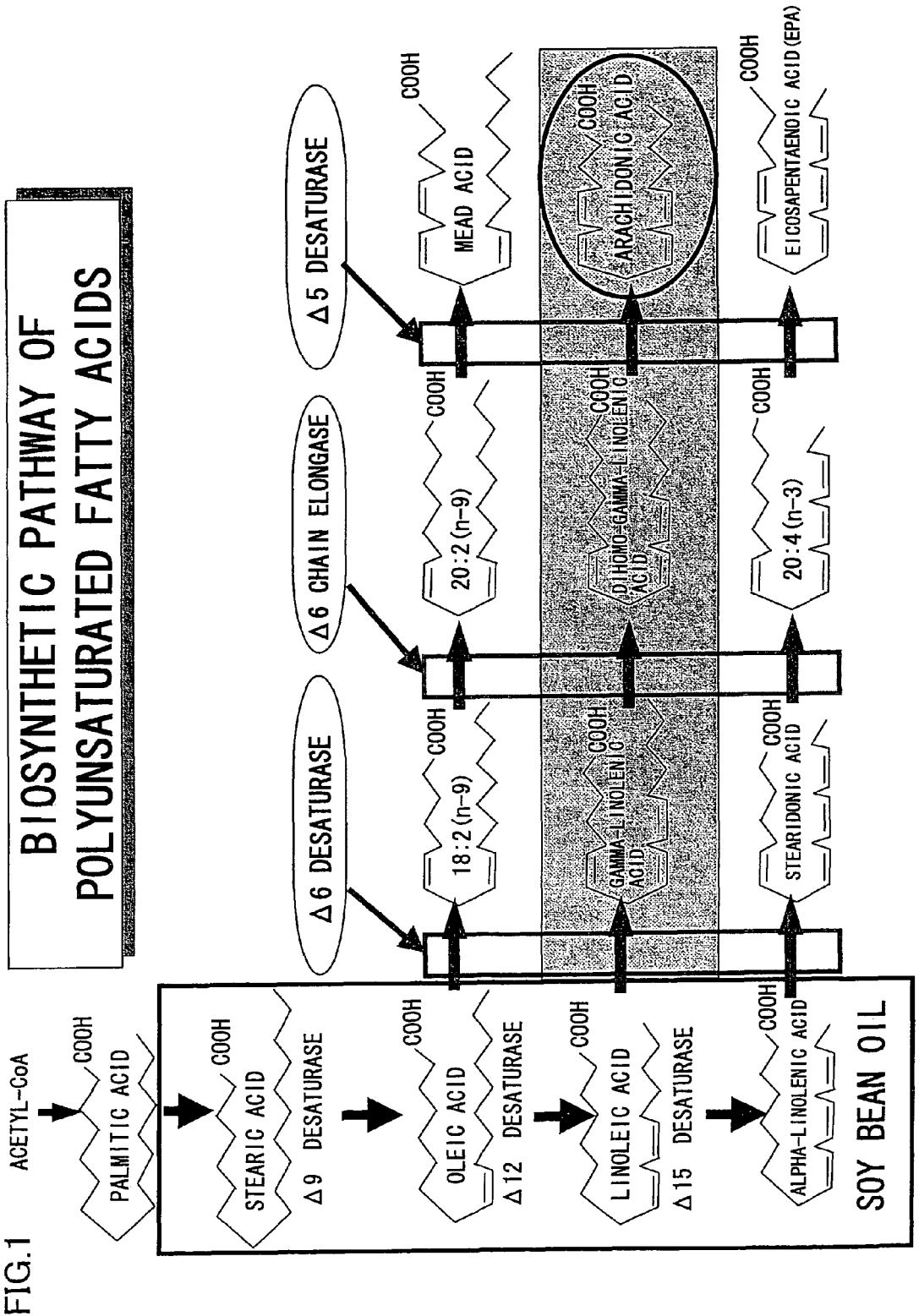
FIG. 1 is a diagram schematically illustrating a biosynthetic pathway of polyunsaturated fatty acids.

The present invention concerns plants and soybeans produced by a process for producing plants or soybeans containing arachidonic acid, which is one of essential PUFAs in higher animals. The invention also concerns use of such plants and soybeans. Before describing the invention in detail, the following will discuss a brief overview of lipid biosynthesis in higher plants in general.

Most lipids in higher plants contain 16 or 18 carbon atoms with 1 to 3 unsaturated bonds. The majority of fatty acids in these lipids are synthesized in the plastids such as the chloroplasts, using acetyl-CoA as a first substrate. In the first reaction involving acetyl-CoA and carbon dioxide, malonyl-CoA is produced by the catalytic action of the acetyl-CoA carboxylase (ACCase). The reaction is one of the rate-determining reactions in the biosynthesis of oil or fat in higher plants, and is believed to influence the level of oil or fat production. In this connection, there has been a report that a total amount of oil or fat produced in rapeseeds was increased by 5% by the overexpression of an ACCase gene (Plant Physiol., 113, p 75-81 (1997)).

The malonyl group of the malonyl-CoA is transferred to ACP to produce a malonyl-ACP. The malonyl-ACP so produced undergoes a series of reactions by repeating condensation, reduction, dehydration, and reduction. In each cycle, the reactions add two carbon atoms to the molecule by the catalytic action of a set of enzymes in a fatty acid synthetase complex, producing a C16:0-ACP or C18:0-ACP in the end. Most of the C18:0-ACPs have a first unsaturated bond at the Δ9 position (after the ninth carbon from the carboxyl end) by the catalytic action of a C18:0-ACP desaturase residing in the plastid.

Some of the C18:1-ACPs are used in the biosynthesis of glycerolipids in the plastids. The others are separated from the ACPs by the catalytic action of the thioesterase, and transported out of the plastid in the form of a CoA ester for the biosynthesis of glycerolipids in the endoplasmic reticulum. That is, the biosynthesis of glycerolipids occurs simultaneously inside and outside of the chloroplasts (mainly in the endoplasmic reticulum if it is outside of the chloroplasts). The biosynthetic pathway of glycerolipids follows that of prokaryotes if it is in the chloroplasts, whereas the glycerolipid biosynthesis taking place outside of the chloroplasts follows the biosynthetic pathway of eukaryotes.

In either biosynthetic pathway, an acyltransferase successively transfers the acyl group to the sn-1 position and sn-2 position of the glycerol triphosphate (G3P), and thereby forms different kinds of glycerolipids with different polar head groups, such as phosphatidylcholine (PC) and phosphatidylglycerol (PG). Some of the lipids, such as PC, synthesized in the eukaryotic biosynthetic pathway become the main constituent of the membrane, while the others transfer the third acyl group to the sn-3 position and become triacylglycerol (TAG), which is the main constituent of depot fat.

The biomenbrane of plants as represented by the soybean is generally rich in linoleic acid and α-linolenic acid. All higher plants contain 18:0-ACP desaturase, Δ12 desaturase, and Δ3 desaturase. The 18:0-ACP desaturase is known to reside in the plastids, whereas the Δ12 desaturase and Δ3 desaturase are both present in the form of at least two isozymes, one in the plastid and the other in the ER. Further, certain species of plants have unique desaturase genes. For example, the Δ6 desaturase of evening primrose or *Borago officinalis* generates γ-linolenic acid from linoleic acid. The Δ5 desaturase of *Limnanthes douglasii* is involved in the synthesis of C20:1 (Δ5).

The majority of fatty acids in plants are C16 or C18. Plants additionally require very long-chain fatty acids with 20 or greater carbon atoms, which occur as the main constituent of the wax covering the body surface, or as a constituent of sphingolipids contained in a large amount in the cell membrane or tonoplast. Further, in some plants, a considerable proportion of C20 or C22 very long-chain fatty acids are contained as the depot fat. The synthetic pathway of the very long-chain fatty acids is similar to that of the de novo synthesis of fatty acids catalyzed by the fatty acid synthetase complex, in the sense that one cycle of condensation, reduction, dehydration, and reduction adds two carbon atoms to the chain. Thus, in the synthetic pathway of the very long-chain fatty acids, the condensation reaction of the existing acyl groups and the malonyl-CoA is also believed to be the rate-determining reaction for elongating the chain.

Contrary to the de novo fatty acid synthesis in which the chain is elongated from the acyl group forming a bond with the ACP, the synthetic pathway of the very long-chain fatty acids does not require ACP for the elongation of the carbon chain. Recently, enzyme genes involved in the first condensation reaction of the chain elongating reaction were obtained from *Arabidopsis thaliana* or *Simmondsia chinensis*. These enzyme genes, specific examples of which are FAE1 (Plant Cell, 7, p 309 (1995)) and KCS gene (Plant Cell, 8, p 281 (1996)), were found to be involved in the synthesis of saturated fatty acids with 20 or greater carbon atoms. It should be noted here that when the fatty-acid-chain elongases of the ELO family found in yeasts, animals, and molds (J. Biol. Chem., 271, p 18413 (1996), J. Biol. Chem., 272, p 17376 (1997)) are compared with the elongases of the FAE1/KCS family in plants, there is no similarity between their primary sequences.

The majority of the depot fats are TAGs, which are generated by the successive acylation of the G3P supplied from the cytoplasm. The three acyl groups in the TAG are transferred to the glycerol skeleton by different acyltransfereases. One of these acyltransferases is lysophosphatidic acid acyltransferase (LPAAT) for transferring the acyl group to the sn-2 position. The LPAAT is generally highly substrate-specific, and is believed to be one of the factors that determines the fatty acid composition of the depot fat.

The TAG is also produced in the synthetic pathway based on PC, which is the predominant lipid synthesized in the eukaryotic synthetic pathway as described above. The TAG is synthesized on the membrane surface of the smooth endoplasmic reticulum, and accumulates in the lipid bilayer membrane. Over time, portions of the lipid bilayer membrane that have accumulated the TAG bulge out and separate from the endoplasmic reticulum by forming a vesicle, also known as oil body, surrounded by a lipid monolayer membrane. Some plants produce a large amount of middle-chain or very long-chain fatty acids with fewer than or greater than 16 or 18 carbon atoms. Others produce a large amount of fatty acids that have been hydroxylated or epoxidized. Most of these unique fatty acids occur in the form of TAG. The mechanism by which the synthetic pathways of these fatty acids are controlled is not all clear, but involvement of a highly substrate-specific phospholipase or acyltransferase has been suggested. This is one of the reasons that makes it difficult to predict the outcome when non-indigenous fatty acids are to be produced in plants at high level. With these backgrounds, the following more specifically describes the present invention.

The present invention relates to oil or fat source plants containing arachidonic acid, and to use of such oil or fat source plants. Oil or fat source plants according to the present invention produce arachidonic acid. The invention therefore provides oil or fat source plants containing arachidonic acid. In the following, a producing process of oil or fat source plants containing arachidonic acid (may be referred to as "arachidonic acid-containing plants") according to the present invention will be described first, followed by oil or fat source plants produced thereby, and use of such oil or fat source plants.

[1] Producing Process of Arachidonic Acid-Containing Plants

A producing process of arachidonic acid-containing plants or soybeans according to the present invention is not particularly limited in terms of steps, conditions, and materials it uses, as long as the process includes the step of producing arachidonic acid by introducing into plants fatty acid synthetase genes associated with the biosynthesis of arachidonic acid. First, "enzymes associated with the fatty acid synthesis" will be described.

[1-1] Enzymes Associated with the Fatty Acid Synthesis

Fatty acid synthetases used in the present invention are, for example, those associated with the biosynthesis of arachidonic acid, non-indigenous to the host plant. Generally, higher plants include a group of enzymes that catalyze the biosynthesis of linoleic acid or α-linolenic acid from stearic acid, but require fatty acid synthetases required for the biosynthesis of arachidonic acid from linoleic acid or α-linolenic acid. Specific examples of such fatty acid synthetases include Δ6 desaturase, fatty-acid-chain elongase (may be referred to simply as "elongase"), and Δ5 desaturase.

As the term is used herein, the "Δ6 desaturase" refers to a protein that catalyzes the reaction in which an unsaturated bond is introduced at the Δ6 position of aliphatic monocarboxylic acids (after the sixth carbon from the carboxyl end). The "fatty-acid-chain elongase" refers to a protein that catalyzes the reaction in which the carbon chains of aliphatic monocarboxylic acids are elongated. The "Δ5 desaturase" refers to a protein that catalyzes the reaction in which an unsaturated bond is introduced at the Δ5 position of aliphatic monocarboxylic acids (after the fifth carbon from the carboxyl end). As used herein, the term "unsaturated bond" refers to a carbon-carbon double bond (C=C). For example, arachidonic acid can be produced in soybeans (*Glycine max*) or other higher plants by ligating genes coding for the three kinds of fatty acid synthetases to a constitutive or seed-specific promoter and introducing the ligated genes into the soybeans or other higher plants.

Higher animals are capable of producing mead acid (C20:3) from stearic acid in their n-9 pathway; however, they cannot synthesize linoleic acid or α-linolenic acid, and therefore require intake of these fatty acids from vegetable oil. On the other hand, some fungi, such as *Mortierella*, and other lower animals such as nematodes have the pathways of both higher plants and higher animals, and are capable of producing arachidonic acid or EPA.

As such, the three kinds of enzymes, the Δ6 desaturase, fatty-acid-chain elongase, and Δ5 desaturase can be obtained from higher animals or microorganism such as *Mortierella*. Among different species of *Mortierella*, filamentous fungi have been used for the fermentation of polyunsaturated fatty acids, and their biosynthesis systems are well studied. Specifically, in the major biosynthetic pathway n-6 of *Mortierella alpina*, arachidonic acid is accumulated via linoleic acid or α-linolenic acid. Note that, in the biosynthetic pathway of arachidonic acid in *Mortierella alpina*, linoleic acid or α-linolenic acid is produced in the same biosynthetic pathway as that of higher plants. In the synthetic pathway producing arachidonic acid from linoleic acid, the linoleic acid is first acted upon by the Δ6 desaturase to produce γ-linolenic acid. Then, the fatty-acid-chain elongase (GLELO) produces dihomo-γ-linolenic acid, which is later converted into arachidonic acid by the Δ5 desaturase.

Genes encoding all enzymes involved in the biosynthetic pathway producing arachidonic acid from stearic acid have been isolated from *Mortierella alpina*. In fact, a gene encoding the Δ5 desaturase (J Biol Chem. 273, p 19055 (1998)), and a gene encoding the fatty-acid-chain elongase that specifically acts on the γ-linolenic acid or stearidonic acid (C18:4) produced by the catalytic action of the Δ6 desaturase (Proc. Natl. Acad. Sci. U.S.A. 97, p 8284 (2000)) are the first genes isolated from *Mortierella alpina*. Note that, among the reactions of condensation, hydroxlation, dehydration, and reduction involved in the elongation of the fatty acid chain, the condensation, the first of the four reactions, is believed to be substrate-specific.

The Δ6 desaturase derived from *Mortierella alpina* is a protein with the amino acid sequence of SEQ ID NO: 1, and it is known to catalyze the reaction of introducing an unsaturated bond at the Δ6 position of aliphatic monocarboxylic acids. It should be noted here that the Δ6 desaturase used in the present invention is not limited to that set forth in SEQ ID NO: 1 as long as it can catalyze the reaction of introducing an unsaturated bond at the Δ6 position of aliphatic monocarboxylic acids. Specifically, the invention can use a protein of an amino acid sequence that has been modified by substitution, deletion, insertion, and/or addition of one or more amino acids of the amino acid sequence of SEQ ID NO: 1, so long as the protein has the foregoing catalytic action. Note that, the number of amino acids that are deleted, substituted, inserted and/or added is not particularly limited. However, for example, 1 to 20 amino acids, preferably 1 to 10 amino acids, more preferably 1 to 7 amino acids, further preferably 1 to 5 amino acids, and particularly preferably 1 to 3 amino acids are substituted, deleted, inserted, and/or added.

The deletion, substitution, or addition of amino acid can be carried out by modifying the peptide-encoding base sequence, using methods known in the art. In order to introduce mutation in the base sequence, the Kunkel method, Gapped duplex method, or other similar known methods can be used. For example, mutation is introduced using a mutation introducing kit (for example, Mutant-K, Mutant-G, both of TAKARA) employing the site-directed mutagenesis inducing method, or the LA PCR in vitro Mutagenesis series kit (TAKARA).

The fatty-acid-chain elongase derived from *Mortierella alpina* is a protein with the amino acid sequence of SEQ ID NO: 3, and it is known to catalyze the reaction of elongating the fatty acid chain of aliphatic monocarboxylic acids. It should be noted here that the fatty-acid-chain elongase used in the present invention is not limited to that set forth in SEQ ID NO: 3, as long as it can catalyze the reaction of elongating the fatty acid chain of aliphatic monocarboxylic acids. Specifically, the invention can use a protein of an amino acid sequence that has been modified by substitution, deletion, insertion, and/or addition of one or more amino acids of the amino acid sequence of SEQ ID NO: 3, so long as the protein has the foregoing catalytic action.

The Δ5 desaturase derived from *Mortierella alpina* is a protein with the amino acid sequence of SEQ ID NO: 5, and it is known to catalyze the reaction of introducing an unsaturated bond at the Δ5 position of aliphatic monocarboxylic acids. It should be noted here that the Δ5 desaturase used in the present invention is not limited to that set forth in SEQ ID NO: 5 as long as it can catalyze the reaction of introducing an unsaturated bond at the Δ5 position of aliphatic monocarboxylic acids. Specifically, the invention can use a protein of an amino acid sequence that has been modified by substitution, deletion, insertion, and/or addition of one or more amino acids of the amino acid sequence of SEQ ID NO: 5, so long as the protein has the foregoing catalytic action.

As will be described later, a producing process of plants according to the present invention can suitably use genes encoding the Δ6 desaturase, fatty-acid-chain elongase, and Δ5 desaturase, using known gene recombinant techniques. A gene that encodes the Δ6 desaturase (may be referred to as "Δ6 desaturase gene" hereinafter) is not particularly limited. For example, when the Δ6 desaturase is derived from *Mortierella alpina*, the enzyme may be encoded by a gene that encodes this particular type of Δ6 desaturase. A specific example of the Δ6 desaturase gene is a polynucleotide having the base sequence of SEQ ID NO: 2 as an open reading frame (ORF).

Evidently, the Δ6 desaturase gene is not limited to the foregoing example, and may be a gene homologous to the base sequence of SEQ ID NO: 2. Specifically, the gene may hybridizes under stringent conditions with a gene having a base sequence complementary to the base sequence of a gene identified by SEQ ID NO: 2, and may encode a protein that catalyzes the reaction of introducing an unsaturated bond at the Δ6 position of aliphatic monocarboxylic acids. As used herein, "under stringent conditions" means that hybridization takes place only when there is at least 90% identity, preferably at least 95% identity, and more preferably at least 97% identity.

Hybridization may be carried out by a conventional method, as described in J. Sambrook et al. Molecular Cloning, A Laboratory Manual, 2nd Ed., Cold Spring Harbor Laboratory (1989), for example. Generally, the level of stringency increases with increase in temperature and/or decrease in salt concentration (more difficult to hybridize).

A gene that encodes the fatty-acid-chain elongase (may be referred to as "fatty-acid-chain elongase gene" hereinafter) is not particularly limited. For example, when the fatty-acid-chain elongase is derived from *Mortierella alpina*, the enzyme may be encoded by a gene that encodes this particular type of fatty-acid-chain elongase. A specific example of the fatty-acid-chain elongase gene is a polynucleotide having the base sequence of SEQ ID NO: 4 as an open reading frame (ORF). Note that, as used herein, the open reading frame is the region from the start codon to the end codon, excluding the end codon.

The fatty-acid-chain elongase gene is not limited to the foregoing example, and may be a gene homologous to the base sequence of SEQ ID NO: 4. Specifically, the gene may hybridize under stringent conditions with a gene having a base sequence complementary to the base sequence of a gene identified by SEQ ID NO: 4, and may encode a protein that catalyzes the reaction of elongating the fatty acid chain of aliphatic monocarboxylic acids.

A gene that encodes the Δ5 desaturase (may be referred to as "Δ5 desaturase gene" hereinafter) is not particularly limited. For example, when the Δ5 desaturase is derived from *Mortierella alpina*, the enzyme may be encoded by a gene that encodes this particular type of Δ5 desaturase. A specific example of the Δ5 desaturase gene is a polynucleotide having the base sequence of SEQ ID NO: 6 as an open reading frame (ORF).

Evidently, the Δ5 desaturase gene is not limited to the foregoing example, and may be a gene homologous to the base sequence of SEQ ID NO: 6. Specifically, the gene may hybridize under stringent conditions with a gene having a base sequence complementary to the base sequence of a gene identified by SEQ ID NO: 6, and may encode a protein that catalyzes the reaction of introducing an unsaturated bond at the Δ5 position of aliphatic monocarboxylic acids.

The method of obtaining the genes is not particularly limited. For example, the genes may be isolated from animals, microorganisms, or plants, using conventional methods. For example, a primer pair may be used that is prepared based on base sequences of known enzymes. The genes can then be obtained by carrying out PCR with the primer pair, using cDNA or genomic DNA of plants as a template. Alternatively, the genes may be chemically synthesized by a conventional method.

[1-2] Exemplary Producing Process of Arachidonic Acid-Containing Soybeans According to the Present Invention A producing process of arachidonic acid-containing soybeans according to the present invention is not particularly limited as long as it includes the step of producing arachidonic acid by introducing into plants the fatty acid synthetase genes described in section [1-1]. For example, a producing process of plants according to the present invention may include a recombinant expression vector constructing step, a transforming step, and a screening step. The present invention requires at least the transforming step. The following describes these steps more specifically.

[1-2-1] Recombinant Expression Vector Constructing Step

A recombinant expression vector constructing step of the present invention is not particularly limited as long as it constructs a recombinant expression vector that includes a promoter (sequence) and genes encoding the fatty acid synthetases described in section [1-1] above.

As the carrier of the recombinant expression vector, various types of conventional vectors, for example, such as a plasmid, a phage, and a cosmid can be used. The vector is suitably selected according to the type of plant cell or introducing method used. Specific examples of the vector include pBR322, pBR325, pUC19, pBluescript, pBluescript SK, and vectors of the pBI family. When the method of introducing a vector into plants employs *Agrobacterium*, binary vectors of the pBI family are preferable. Specific examples of such binary vectors include pBIG, pBIN19, pBI101, pBI121, and pBI221.

The promoter is not particularly limited as long as it can express the genes in plants, and known promoters can be suitably used. Specifically, the promoter may be, for example, a cauliflower mosaic virus 35S promoter (CaMV35S), an actin promoter, a nopaline synthetase promoter, a tobacco PR1a gene promoter, or a tomato ribulose-1,5-diphosphate carboxylase/oxygenase small subunit promoter. Among these promoters, the cauliflower mosaic virus 35S promoter and the actin promoter are preferable. Further, as a functional promoter in soybeans, a promoter for the storage protein conglycinin of soybean seeds can be suitably used. Further, the promoter may be a constitutive promoter, or a tissue-specific promoter. With the use of these promoters, the recombinant expression vector can express a desired gene at high level when introduced into a plant cell. Among the foregoing promoters, seed-specific promoters are preferable. Specifically, it is preferable that genes encoding the fatty acid synthetases associated with the biosynthesis of arachidonic acid be ligated downstream of the seed-specific promoter. More specifically, the Δ6 desaturase, the fatty-acid-chain elongase, and Δ5 desaturase may be ligated downstream of their respective promoters. As a soybean seed-specific promoter, a conglycinin promoter may be used for example, as will be described later in Examples. In this way, enzymes associated with the biosynthesis of arachidonic acid can be expressed both efficiently and stably, thereby realizing stable production of arachidonic acid.

The recombinant expression vector is not limited to a specific structure as long as a promoter is so ligated therein as to express the genes encoding the fatty acid synthetases described in section [1-1] above.

In the event where the fatty acid synthetases expressed in a host plant are Δ6 desaturase, fatty-acid-chain elongase, and Δ5 desaturase, the plant may be transformed using a recombinant expression vector that has incorporated all of these three enzyme genes for their expression. Alternatively, the Δ6 desaturase, fatty-acid-chain elongase, and Δ5 desaturase may be respectively incorporated in different vectors, and may be separately expressed in the host plant cell after they are introduced into the host plant together. However, the use of the recombinant expression vector that has incorporated the three kinds of enzyme genes is more preferable. When using a recombinant expression vector that has incorporated the Δ6 desaturase, fatty-acid-chain elongase, and Δ5 desaturase genes, it is preferable that the genes encoding these enzymes are so ligated as to be transcribed all in the same direction. However, the genes may be so ligated as to be transcribed in opposite directions as long as they are expressed in the host plant.

In addition to the promoter and the fatty acid synthetase genes, the recombinant expression vector may further include other DNA segments. Non-limiting examples of such DNA segments include a terminator, a selection marker, an enhancer, and a base sequence for improving translation efficiency. Further, the recombinant expression vector may also include a T-DNA region. With the T-DNA region, the efficiency of gene intake can be improved when *Agrobacterium* is used to introduce the recombinant expression vector into the plant.

The terminator is not particularly limited as long as it serves as a terminal site of transcription, and known terminators may be used. Preferable examples include: a transcription terminal site of the nopaline synthetase gene (Nos terminator); a transcription terminal site of the cauliflower mosaic virus 35S (CaMV35S terminator), and a transcription terminal site of the mannopine synthetase gene (Mas terminator). Among these examples, the Nos terminator or Mas terminator is more preferable.

With the terminator placed in an appropriate position, synthesis of unnecessarily long transcripts can be prevented in the recombinant expression vector. Further, the terminator prevents a strong promoter from reducing the number of plasmid copies.

As the selection marker, a drug resistant gene may be used, for example. Specific examples include genes resistant to hygromycin, bleomycin, kanamycin, gentamicin, and chloramphenicol. With the use of these genes, plants growing in media containing these antibiotics can be screened, allowing for easy selection of transformed plants.

One example of the base sequence for improving translation efficiency is an omega sequence derived from the tobacco mosaic virus. By placing the omega sequence in the non-translation region (5' UTR) of the promoter, the translation efficiency of the chimera gene can be improved. In this manner, the recombinant expression vector may incorporate various types of DNA segments depending on its intended use.

The method of constructing the recombinant expression vector is not particularly limited either. In one example, the promoter, genes encoding the fatty acid synthetases, and optionally other DNA segments are incorporated in a predetermined order into a suitably selected carrier vector. Specifically, three genes respectively encoding the Δ6 desaturase, fatty-acid-chain elongase, and Δ6 desaturase are ligated to one another in such a manner as to enable their expression, and these fatty acid synthetase genes are ligated to the promoter (and optionally to a terminator or other DNA segments) so as to construct an expression cassette, which is then introduced into a vector. Note that, as mentioned above, the three genes are not necessarily required to be placed in the same vector. For example, the three genes may be placed in different vectors.

In the construction of the fatty acid synthetases and the expression cassette, the order of the DNA segments can be specified by providing complementary cohesive ends for the DNA segments and by carrying out the reaction of these DNA segments with a ligase. When the expression cassette includes a terminator, the terminator is placed downstream of the promoter and the fatty acid synthetases. The type of reagent, for example, such as a restriction enzyme or ligase, used for the construction of the recombinant expression vector is not particularly limited. Any commercially available reagent may be suitable selected.

The method of proliferating (producing) the recombinant expression vector is not particularly limited either, and any conventional method can be used. Generally, *Escherichia coli* is selected as a host. In this case, the type of *E. coli* may be suitably selected according to the type of vector used.

[1-2-2] Transforming Step

In the transforming step used in the present invention, the recombinant expression vector described in section [1-2-1] above is introduced into a plant cell to produce the fatty acid synthetases described in section [1-1] above.

The method of introducing the recombinant expression vector into a plant cell is not particularly limited, and conventional methods can be suitably used according to the type of plant cell. Specifically, a method using Agrobacterium, or a method in which the recombinant expression vector is directly introduced into a plant cell may be used, for example. As a method using *Agrobacterium*, Transformation of *Arabidopsis thaliana* by vacuum infiltration may be used, for example.

The method of directly introducing the recombinant expression vector into a plant cell may be, for example, a microinjection method, an electroporation method, a polyethylene glycol method, a particle gun method, a protoplast cell fusion method, or a calcium phosphate method.

Examples of host plant cells of the recombinant expression vector include cells of various tissues of flowers, leaves, roots, or other plant organs. Other examples include callus, and cells in a suspension culture.

In a producing process of plants according to the present invention, the recombinant expression vector may be suitably constructed according to the type of plant to be produced. Alternatively, the recombinant expression vector may be a multi-purpose vector that can be introduced into a plant cell. In sum, a producing process of plants according to the present invention may or may not include the recombinant expression vector constructing step described in section [1-2-1] above.

In the case where the host plant includes a Δ15 desaturase, it is preferable that the expression of this enzyme be suppressed. As shown in FIG. 1, the Δ15 desaturase converts the linoleic acid, produced in the soybeans, into α-linolenic acid. It is therefore preferable to suppress the expression of the Δ15 desaturase, in order to convert all of the linoleic acid, produced in the soybeans, into γ-linolenic acid, which is the precursor of arachidonic acid. The method of suppressing the expression of Δ15 desaturase is not particularly limited, and conventional genetic engineering techniques may be used, including the anti-sense method, the sense method (cosuppression method), and the RNAi method in which double-stranded RNA is transcribed. Among these methods, the RNAi method is preferable, as will be described later in Examples. With the RNAi method, the expression of the Δ15 desaturase can be suppressed both easily and reliably. That is, it is preferable that the arachidonic acid producing step of the invention include the expression suppressing step of suppressing the Δ15 desaturase expression in a host. It is also preferable that the expression suppressing step uses the RNAi method to suppress the Δ15 desaturase expression.

[1-2-3] Other Steps and Methods

A producing process of plants according to the present invention includes the transforming step, and, additionally, the recombinant expression vector constructing step. In addition to these steps, the process may include other steps. One specific example of such a step is a screening step for screening for suitable individuals from transformed plants.

The method of screening is not particularly limited. For example, screening may be based on drug resistance such as hygromycin resistance. Alternatively, screening may be made based on the arachidonic acid content in the transformed plants themselves, or in particular organs or tissues of the transformed plants. Further, screening may be made by visually confirming fluorescent proteins, such as GFP, that were introduced when transforming the plants.

A producing process of plants according to the present invention introduces the fatty acid synthetase genes in plants. Thus, once arachidonic acid-containing plants are obtained by transformation, their offspring can readily be reproduced either sexually or asexually (e.g., using calluses). The plants or their offspring may be used to obtain seeds, fruits, stumps, callus, tubers, cuttings, clumps, or other sources of reproduction, so as to mass produce the plants from these sources. As such, a producing process of plants according to the present invention may also include a reproducing (mass-producing) step of reproducing selected plants.

Note that, as used herein, the term "plants" mean at least one of the following entities: grown plant individuals, plant cells, plant tissues, callus, and seeds. Further, the invention also includes offspring of the plants reproduced by the reproducing step. That is, the present invention includes all forms of plants that can grow into plant individuals. Further, as used herein, the term "plant cells" means various types of plant cells, including cells in a suspension culture, propoplasts, and slices of leaves, for example. The plants can be obtained by proliferating and differentiating these plant cells. Note that, the plant cells can regenerate plants according to conventional methods, depending on the type of plant cell used. As such, a producing process of plants according to the present invention may include a regenerating step of regenerating plants from plant cells.

Further, a producing process of plants according to the present invention is not just limited to the transformation using a recombinant expression vector, but may be carried out in different ways. For example, the fatty acid synthetases may be directly administered to plants. For example, the fatty acid synthetases may be administered to a young plant so that required portions of the plant contain arachidonic acid when they are used. The administration method of the fatty acid synthetases is not particularly limited either, and various conventional methods can be used.

[2] Arachidonic Acid-Containing Plants and Soybeans According to the Present Invention, and Usefulness and Use Thereof In a producing process of arachidonic acid-containing plants and soybeans according to the present invention, the fatty acid synthetase genes associated with the biosynthesis of arachidonic acid is introduced into plants or soybean. The fatty acid synthetase genes associated with the synthesis system of arachidonic acid are expressed in the soybeans, and arachidonic acid is produced in the biosynthetic pathway that is not found in higher plants in nature. Thus, the plants so produced contain arachidonic acid. The present invention therefore provides arachidonic acid-containing plants and soybeans produced by the producing process of plants as described above.

[2-1] Usefulness of the Present Invention

While the invention produces arachidonic acid in plants, usefulness of the invention is not limited. For example, plants containing arachidonic acid may be directly marketed as agricultural products or food products. Alternatively, arachidonic acid may be extracted from the plants for use. The present invention therefore provides arachidonic acid obtained from plants produced by the producing process of the present invention.

The method of extracting arachidonic acid from oil or fat source plants containing arachidonic acid is not particularly limited, and conventional extraction and purification methods can be used. For example, arachidonic acid may be separated and purified from oil that was obtained like soybean oil by squeezing the transformed soybeans.

Further, as will be described later in Examples, it was confirmed by experiments that the modified trait of transformed soybeans according to the present invention is passed onto the next generation. This means that soybeans containing arachidonic acid can be mass produced by cultivating transformed soybeans according to the present invention. The present invention is therefore industrially highly useful.

As described above, arachidonic acid is known to exhibit various functions in the body of animals. Further, the role of arachidonic acid as a direct precursor of prostaglandins is also known to be important. Furthermore, arachidonic acid has been shown to be effective for senile dementia. This enables the arachidonic acid-containing plants, and the arachidonic acid obtained therefrom to be applied to compositions (for example, oil or fat compositions) food (health food, etc.), or medicines for improving senile dementia. As used herein, the meaning of the term "composition" is not particularly limited, and the "composition" may contain components other than arachidonic acid. For example, PUFA such as PC, DHA, and EPA may be contained other than arachidonic acid. Further, as used herein, the term "food" is not particularly limited as long as it can be orally ingested. For example, food may be in the form of a tablet, a liquid, or a powder. Specifically, an oil or fat composition containing arachidonic acid may be encapsulated in a capsule that is soluble in the body, so as to provide health food.

[2-2] Use of the Present Invention

The present invention is not limited to a particular application or a particular method of use. For example, the present invention may be used to provide a kit for performing a producing process of plants according to the present invention, namely, an arachidonic acid-containing plant preparation kit.

Specifically, such an arachidonic acid-containing plant preparation kit includes at least a recombinant expression vector containing genes for encoding the fatty acid synthetases, and preferably a set of reagents for introducing the recombinant expression vector into the plant cell. Examples of such reagents include enzymes and buffers that are selected according to the type of transformation. As required, the arachidonic acid-containing plant preparation kit may optionally include experiment instruments such as a micro centrifugal tube.

With an arachidonic acid-containing plant preparation kit according to the present invention, a producing process of plants according to the present invention can readily be performed, thereby producing arachidonic acid-containing plants both easily and reliably.

While the invention is susceptible to various modifications and alternative forms, a specific embodiment thereof will be described below in more detail by way of Examples with reference to the attached drawings. It should be understood, however, that it is not intended to limit the invention to the particular forms disclosed, but on the contrary, the invention is to cover all modifications, equivalents, and alternatives falling within the scope of the invention as defined in the appended claims.

EXAMPLES

[I] Analysis of Fatty Acids

Extraction and analysis of lipids were carried out according to the publicly known methods (Yasuhiko FUJINO, "*Seibutsu-Kagaku Jikken-ho*" (Method of Biochemical Experiment) 9, Gakkai Shuppan Center (1978); Akihiro YAMADA, "*Seibutsu-Kagaku Jikken-ho*" (Method of Biochemical Experiment) 24, Gakkai Shuppan Center (1989)). First of all, one leaf of a transformant tobacco cultivated in a containment greenhouse was cut off at the base. After being weighed, the cut leaf was washed with water and cut into 5 mm square small pieces using a pair of scissors. About 1 g of the small pieces of leaves was put into a stainless-steel cup of 50 ml capacity. 35 ml of chloroform/methanol (1:2) solution and 7.5 ml of glass beads (diameter: 0.4 mm) were added into the cup, and the pieces of leaves were subjected to rotation at 10000 rpm for 10 minutes by a homogenizer (CELL MASTER CM-100, IUCHI SEISAKUSHO).

The contents in the cup were filtered with a filter paper, and the filter cake were repeatedly washed with chloroform/methanol (1:2) solution and filtered until 90 ml of filtrate was obtained. 22.5 ml of the filtrate was separately injected into each glass centrifuging tube of 50 ml capacity, and 7.5 ml of chloroform and 13.5 ml of 1% KCl aqueous solution were added to the each centrifuging tube. After being vigorously mixed for 10 minutes, the mixture was centrifuged at 3000 rpm for 20 minutes. The solution was divided into two layers, and the lower layer of the two layers, chloroform layer, was collected. The chloroform layer was moved into a screw-top tube ($\phi$ 16 mm×125 mm) which was weighed in advance, and its solvent was removed by evaporation by using a speedvac (SC210, SAVANT). The screw-top tube was weighed and a volume of collected lipids was calculated from the weight of the screw-top tube.

Two ml of 10% hydrochloric acid in methanol and 1 ml of dichloromethane were added to about 4 mg of lipid in the screw-top tube. After the screw-top tube was covered with a lid, the solution in it was heated at 50° C. for 3 hours to convert the lipid into fatty acid methyl ester. After the reaction, 1 ml of distilled water and 4 ml of hexane were added thereto, and the mixture was vigorously mixed for 5 minutes and centrifuged at 3000 rpm for 5 minutes. The upper layer, hexane layer, was collected into another tube and evaporated until hexane was removed, using a speedvac. After this operation was repeated twice, fatty acid methyl ester was collected. Fatty acid methyl ester was dissolved in 50 µl of acetonitrile and analyzed by gas chromatography (Hewlett Packard, HP-6800). Table 1 shows the analysis condition.

TABLE 1

| Gas chromatography analysis condition | |
|---|---|
| Column | Supelco SP-2330, Fused Silica Capillary Column, 30 m × 0.32 mm ID, 0.2 µm |
| Temperature | Inj: 240° C., Det: 250° C., Oven: 180° C. for 3 min, 180° C. → 220° C. (2° C./min) |
| Flow rate of column | 30 cm/sec, Pressure: 200 kPa, Detector: FID |

Each peak in chromatogram was determined based on a retention time of methyl ester of standard fatty acids, and GC-MASS (Hewlett Packard, HP-5973) analysis. The proportions of the respective fatty acids were determined by the peak areas.

[II] Expression of *Mortierella Alpina*-Derived Genes in Tobacco

[II-1] Expression of Δ6 Desaturase Gene

A plasmid vector pE2113 (Plant Cell Physiol. 37, p 45 (1996)) was used which contained a cauliflower mosaic virus 35S (E1235S) promoter where enhancer sequences are repeated, and a nopaline synthase (nos) terminator. The pE2113 was digested with SnaBI, followed by insertion of an XhoI linker (TAKARA), to obtain a plasmid. The plasmid was digested and blunted with SacI, and a BamHI linker (TAKARA) was inserted to obtain pUE7.

Of the DNA fragments obtained from the digestion of pUE7 with HindIII and EcoRI, a fragment having a E1235S promoter was ligated to a plant transforming binary vector pBINPLUS (Transgenic research 4, p 288, (1995)) digested with HindIII and EcoRI, so as to obtain pSPB505. Meanwhile, a plasmid PMLD101 containing Δ6 desaturase gene derived from *Mortierella* was digested with XhoI followed by partial digestion with BamHI, and an about 1.6 kb DNA fragment was collected. The DNA fragment was ligated to another DNA fragment of a binary vector obtained from digestion of pSPB505 with XhoI and BamHI, so as to obtain pSPB559. In this plasmid, the Δ6 desaturase gene derived from *Mortierella* was under the control of the E1235S promoter and the nos terminator.

Based on the known method (Plant J. 5, 81, (1994)), pSPB559 was introduced into *Agrobacterium*, and the recombinant *Agrobacterium* was introduced into tobacco. Based on the known method (Plant J. 5, 81, (1994)), RNA was extracted from leaves of the recombinant tobacco, and lines which expressed the *Mortierella*-derived Δ6 desaturase gene were selected by Northern hybridization. Fatty acids in the tobacco leaves were analyzed by the method described in the section [I] above. The analysis showed that 1.8% to 7.3% of γ-linolenic acid, not contained in a host tobacco, was present in the recombinant tobacco leaves. From this result, it was found that the Δ6 desaturase gene derived from *Mortierella* can function in plants.

[II-2] Co-Expression of Δ6 Desaturase Gene and Fatty-Acid-Chain Elongase Gene

A vector pUCAP (Transgenic research 4, p 288, (1995)) was digested and blunted with AscI, and a PacI linker was inserted to obtain pUCAPP. By digesting pE2113 with SnaBI and inserting a BamHI linker (TAKARA), pUE6 was obtained. This pUE6 was digested and blunted with SacI, and a SalI linker (TAKARA) was inserted to obtain pUE8.

Of the DNA fragments obtained by the digestion of pUE8 with HindIII and EcoRI, a fragment having E1235S promoter was inserted into a HindIII-EcoRI site of pUCAPP. A DNA fragment obtained by the digestion of this plasmid with BamHI and SalI was ligated to a DNA fragment obtained by the digestion of chain elongase cDNA with BamHI and XhoI, so as to obtain pSPB1130. The plasmid pSPB1130 was digested with PacI, and a resulting DNA fragment of about 2.3 kb was inserted into a PacI site of pBinPLUS. Plasmids that had the same transcription direction for the chain elongase gene and the nptII gene on the pBinPLUS were selected to obtain pSPB1157P.

Further, pSPB599 was digested and blunted with PacI, and an AscI linker was inserted to obtain pSPB599A. The pSPB599A was digested with AscI, and a DNA fragment containing the Δ6 desaturase gene, obtained by the digestion of pSPB599A with AscI, was inserted into an AscI site of pSPB1157P to obtain pSPB1157.

The binary plasmid pSPB1157 was introduced into a tobacco in the manner as described above to obtain a transformant tobacco. As a result, in the tobacco leaves in which the chain elongase gene and Δ6 desaturase gene were expressed, 0.1% to 5% of the total fatty acids was confirmed to be dihomo-γ-linolenic acid. On the other hand, dihomo-γ-linolenic acid was not present in non-transformed host tobacco leaves. From the result, it was found that the Δ6 fatty acid desaturase and the fatty-acid-chain elongase were co-expressed and became functional in the transformed tobacco prepared by using the binary plasmid that had the Mortierella-derived Δ6 fatty acid desaturase gene and the fatty-acid-chain elongase gene on the same vector

[II-3] Co-Expression of Δ6 Desaturase Gene, Fatty-Acid-Chain Elongase Gene, and Δ5 Desaturase Gene An about 1.3 kb DNA fragment obtained by digestion of pCGP1364 (Plant Cell Physiol. 36, p 1023, (1995)) with HindIII and SacII was ligated to an about 2.9 kb DNA fragment obtained by digesting pCGP1364 with PstI, blunting it, and further digesting it with SacII. These DNA fragments were further ligated to an about 2.7 kb DNA fragment obtained by digesting pUCAPA with SacI, blunting it, and further digesting it with HindIII, so as to obtain pSPB184. A DNA fragment obtained by digesting the pSPB184 with XbaI and KpnI was ligated to a DNA fragment obtained by digesting a fragment of Δ5 desaturase gene, subcloned into pCR2, with XbaI and KpnI, so as to obtain pSPB1519A.

The pSPB1519A was digested with AscI and inserted into an AscI site of pSPB1157 to obtain pSPB1519. In the plasmid pSPB1519, the fragments of ptII, Δ5 desaturase gene, chain elongase gene, and Δ6 desaturase gene were all transcribed in the same direction, and the Δ5 desaturase gene, chain elongase gene, and Δ6 desaturase gene were under the control of a constitutive promoter.

In the same manner as described above, a transformant tobacco was obtained using pSPB1519, and individuals which expressed the Δ5 desaturase gene, chain elongase gene, and Δ6 desaturase gene were identified. An analysis of fatty acids in the transformant tobacco leaves found no presence of arachidonic acid. The analysis result, which shows the evidence of transcription for the Δ5 desaturase gene, chain elongase gene, and Δ6 desaturase but no evidence of arachidonic acid synthesis, indicates that the transcription of the Δ5 desaturase gene, chain elongase gene, and Δ6 desaturase gene by itself is not sufficient for the arachidonic acid production.

[II-4] Function Confirmation of Δ5 Desaturase Gene

As described earlier, the transformant tobacco leaves did not produce arachidonic acid, although the Δ5 desaturase gene was transcribed. Feasible reasons for this result are (i) insufficient level of dihomo-γ-linolenic acid that provides a substrate for the Δ5 desaturase and (ii) inactivity of the Δ5 desaturase.

In view of this, the pSPB1519-transformed tobacco was analyzed to see if it produces arachidonic acid with externally supplied dihomo-γ-linolenic acid. The analysis was carried out according to the method of Qiu et al. (J. Biol. Chem. 276, p 31561 (2001)). That is, 1 g of fresh tobacco leaf was cut into small pieces using a razor blade and was gently cultivated by shaking with 10 ml of 0.05% dihomo-γ-linolenic acid sodium aqueous solution at 24° C. for 4 hours in a Petri dish. After the cultivation, the sample was washed with water three times, and the fatty acids were analyzed.

As a result, from the analysis using two lines of transformants, it was confirmed that the pSPB1519-transformed tobacco synthesized arachidonic acid when cultivated with dihomo-γ-linolenic acid, suggesting that the Δ5 desaturase was functional in the tobacco leaf. This result indicates that the absence of arachidonic acid production in the pSPB1519-transformed tobacco was indeed due to an insufficient level of dihomo-γ-linolenic acid that provides a substrate for the Δ5 desaturase.

[III] Transformation of Soybean

Soybeans (Glycine max) were cultivated basically according to the method of Finer et al. (In vitro Cell. Dev. Biol. Plant 35:451 (1999)), and a somatic embryo of Jack-bean immature cotyledon (3 mm to 5 mm) was induced in an induction culture medium (30 g/l sucrose, 40 mg/l 2,4-D, B5 vitamins-added MS culture medium, pH 7.0).

After the induced somatic embryo was grown in a liquid growth culture medium (10 g/l sucrose, 1 g/l asparagine, 5 mg/l 2,4-D, FNLite culture medium, pH 5.8), a gene was introduced into the induced somatic embryo by the particle gun method (gold particle of 1.0 μm diameter and rapture disk of 1350 dpi). After the transgenic somatic embryo was cultivated in a growth culture medium for one week, selection was made for one month in three growth culture media containing 15 mg/l of hygromycin, 30 mg/l of hygromycin, and 45 mg/l of hygromycin, respectively, and the selected embryos were transplanted to an aqueous differentiation and maturation culture medium (30 g/l sucrose, 30 g/l D-Glucitol, 298.4 mg/l L-methionine, 4.38 g/l L-glutamin, FNLite culture medium, pH 5.8) for re-differentiation. In the differentiation and maturation culture medium, the embryos gradually grew (at this stage, still immature embryos), and matured into mature embryos by differentiating into a distinct cotyledon and hypocotyl as they developed. The mature somatic embryo was dried and germinated in a germination culture medium, and a complete plant was obtained. Note that, the liquid shaking cultivation was carried out at 100 rpm using a rotating shaker.

[IV] Improvement of Multigene Expression Vector

The majority of restriction enzyme recognition sites in the existing vectors are 6-base restriction enzyme recognition sites. When a plurality of expression cassettes each of which is made up of a target gene combined with a promoter and a terminator are inserted into a single vector, there are cases where the restriction enzyme recognition site cannot be used due to the presence of a recognition site in the target gene. One possible solution for such a problem is to use an 8-base restriction enzyme recognition site. Accordingly, a vector was prepared which contained four additional 8-base restriction enzyme recognition sites, as described below in detail.

First of all, pUCAP having two 8-base recognition sites was digested with AscI, and an SgfI linker was inserted. The plasmid was further digested with PacI, and an FseI linker was inserted to prepare a plasmid pUCSAPF having four 8-base recognizing restriction enzyme recognition sites. In addition, for subcloning, four other plasmids were prepared: pUCSA obtained by digesting pUC19 with HindIII, followed by insertion of an SgfI linker, and further digesting it with EcoRI, followed by insertion of an AscI linker; pUCPF obtained by digesting pUC19 with HindIII, followed by insertion of a PacI linker, and further digesting it with EcoRI, followed by insertion of an FseI linker; pUCSS obtained by digesting pUC19 with HindIII, followed by insertion of an SgfI linker, and further digesting it with EcoRI, followed by insertion of an SgfI linker; and pUCFF obtained by digesting pUC19 with HindIII, followed by insertion of an FseI linker, and further digesting it with EcoRI, followed by insertion of an FseI linker.

[V] Construction of a Plant Expression Vector of Fatty Acids Synthetase Genes

In order to provide an arachidonic acid-producing vector, a plant expression vector of fatty acids synthetase genes was prepared by combining an expression cassette containing the Δ6 desaturase, fatty-acid-chain elongase (GLELO), and Δ5 desaturase, all derived from *Mortierella*, with an RNAi cassette of the Δ15 desaturase derived from soybeans, along with a seed-specific promoter. For the seed-specific promoter, a soybean conglycinin alpha' subunit promoter (Proc. Nat. Acad. Sci. USA, 83 p 8560 (1986)) was used. Specifically, the plant expression vector of fatty acids synthetase genes was constructed in the following manner.

First, a conglycinin promoter amplified by PCR, treated with restriction enzymes, and purified was inserted between HindIII and XbaI in the multiple cloning site of pUC19. Similarly, a mannopine synthetase gene terminator amplified by PCR, treated with restriction enzymes, and purified was inserted between SacI and EcoRI in the multiple cloning site of pUC19 (pSPB1904). In the PCR reaction, a plasmid subcloning a target sequence was used as a template. For the conglycinin promoter used in PCR, primers HinCprof (5'-AGTCAAGCTTAATTCAAACAAAAACG-3') (SEQ ID NO: 7) and XbaCpror (5'-CAGTTCTAGAAAATTCTTTAATACGG-3') (SEQ ID NO: 8) were used. For the mannopine synthetase gene terminator, primers Sacmasf (5'-AGTCGAGCTCCAGCTTCCCTGAAACC-3') (SEQ ID NO: 9) and Ecomasr (5'-CATCATCTCGAGGGTGGTGACCATGGTGATCGC-3') (SEQ ID NO: 10) were used.

All the PCR-amplified DNA fragments used for subcloning were prepared using a KOD-plus-polymerase (Toyobo Co., Ltd.) that provides accurate DNA amplification, by first maintaining the DNA fragments at 94° C. for two minutes, and then by performing a PCR reaction in 25 cycles at 94° C. for 15 seconds and at 68° C. for 1 to 3 minutes. After the PCR, each DNA fragment of the Δ5 desaturase, Δ6 desaturase, and fatty-acid-chain elongase was subcloned between XbaI and SacI of pSPB1904 to provide pSPB1909, pSPB1910, and pSPB1911, respectively.

A Δ5 desaturase cassette obtained by digesting pSPB1909 with HindIII and EcoRI was inserted into pUCSA. Similarly, a chain elongase cassette obtained by digesting pSPB1911 with HindIII and EcoRI was inserted into pUCPF. These plasmids are referred to as pSPB1919 and pSPB1920, respectively. Further, a Δ5 desaturase cassette obtained by digesting the pSPB1919 with PacI and FseI, a fatty-acid-chain elongase cassette obtained by digesting the pSPB1920 with SgfI and AscI, and a Δ6 desaturase cassette obtained by digesting the pSPB1910 with HindIII and EcoRI were incorporated in pUCSAPF to prepare a three-cassette plasmid pSPB1944.

Further, an HPT cassette containing a 35S promoter, a hygromycin-resistant gene, and a nos terminator was subcloned into the HindIII site of pUCFF, and a GFP cassette containing a 35S promoter, a green fluorescent protein, and a nos terminator was subcloned between SphI and EcoRI of pUCSS, so as to prepare pSPB1918 and pSPB1935, respectively. Still further, an HPT cassette excised from the pSPB1918 was inserted into the FseI site of pPSB1944, and a GFP cassette excised from the pSPB1935 was inserted into the SgfI site. As a result, pSPB1852 was prepared.

Further, for subcloning of the Δ15 desaturase gene (Accession No. P 48625), RT-PCR was carried out using a total RNA extracted from soybean immature seeds. More specifically, the RT-PCR was carried out in the following manner.

A reverse transcription reaction was carried out with Oligo (dT)12-18 primers, using a SuperScript First-Strand Synthesis System for RT-PCR (Invitrogen). Using a resulting transcript as a template, a PCR reaction was carried out using primers det15-2-F1 (5'-ATGGTTAAAGACACAAAGCCTTTAGCC-3') (SEQ ID NO: 11) and det15-2-R1 (5'-TCAGTCTCGTTGCGAGTGGAGG-3') (SEQ ID NO: 12).

The PCR reaction was carried out by maintaining the sample at 94° C. for two minutes, and then by allowing the reaction in 30 cycles at 94° C. for 30 seconds, at 55° C. for 30 seconds, and at 72° C. for 30 seconds to 1 minute, and finally by maintaining the sample at 72° C. for one minute. The amplified DNA fragments were subcloned into a pCRII vector using a TOPO cloning kit (Invitrogen), and its sequence was determined. For the subcloned Δ15 desaturase gene, a DNA fragment, starting from 5 bases downstream of the start codon and ending at 591 bp, was joined to BamHI and XhoI recognition sequences, and a DNA fragment, starting from 5 bases downstream of the start codon and ending at 791 bp, was joined to SacI and XhoI recognition sequences. These DNA fragments were PCR-amplified and purified.

As the primers, SOYF1-B (5'-TGGCCTGGGATCCTTAAAGACACAAAGCCTTTA-3') (SEQ ID NO: 13) and SOYR1-X (5'-GCACATCTCGAGGGATTGAAGTGAGAGCCTTC-3') (SEQ ID NO: 14) were used for the approximately 591 bp fragment. For the approximately 791 bp fragment, primers SOYF2-S (5'-GTCTGCGAGCTCTTAAAGACACAAAGCCTTTA-3') (SEQ ID NO: 15) and SOUR2-X (5'-CATCATCTCGAGGGTGGTGACCATGGTGATGC-3') (SEQ ID NO: 16) were used.

These two types of DNA fragments were inversely joined to each other with BamHI-XhoI-SacI, so as to form a hairpin structure, and were inserted into a BamHI-SacI site between the conglycinin promoter and the nos terminator to prepare an RNAi cassette (pSPB1876). A Δ15 RNAi cassette was excised from the pSPB1876 and was inserted into an AscI site of pSPB1852 to prepare pSPB1877.

Figure 2:
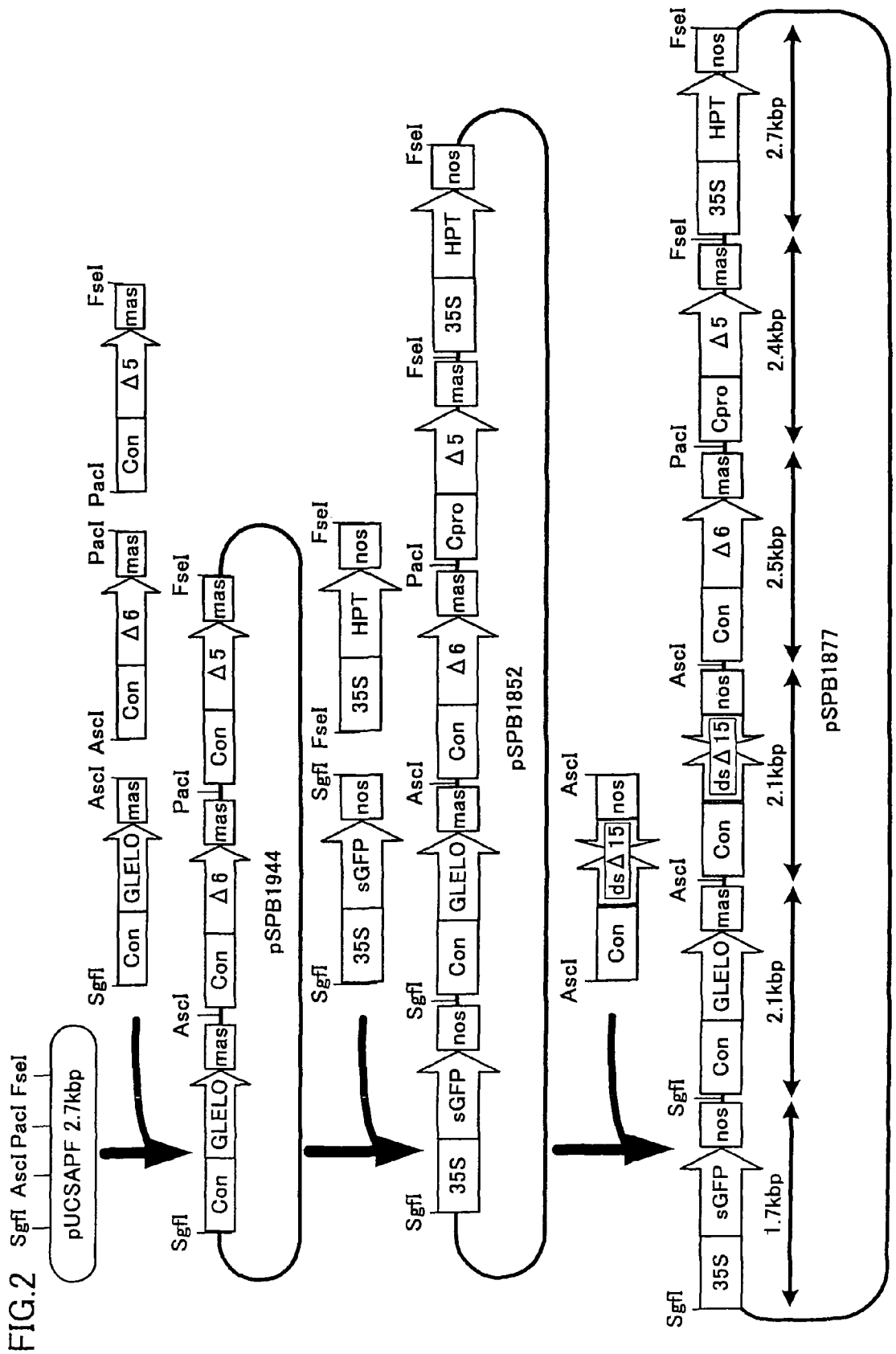
FIG. 2 is a diagram schematically illustrating preparation steps of plasmid vector pSPB1877 according to the present invention.

The pSPB1877 can also be prepared in the steps illustrated in FIG. 2. Specifically, a GLELO gene fragment, a Δ6 desaturase gene fragment, and a Δ5 desaturase fragment are introduced into the SgfI-AscI site, AscI-PacI site, and PacI-FseI site, respectively, of a 2.7 kbp pUCSAPF, so as to prepare pSPB1944. Here, the GLELO gene fragment is a fragment in which GLELO cDNA is ligated between a conglycinin promoter represented by "Con" in FIG. 2 and a mannopine synthetase gene terminator represented by "mas" in FIG. 2. The Δ6 desaturase gene fragment is a fragment in which Δ6 desaturase cDNA is ligated between Con and mas. The Δ5 desaturase gene fragment is a fragment in which Δ5 desaturase cDNA is ligated between Con and mas. The pSPB1944 was then treated with SgfI and FseI, so as to introduce a GFP cassette containing a 35S promoter, a green fluorescent protein, and a nos terminator into the SgfI site, and a HPT cassette containing a 35S promoter, a hygromycin-resistant gene, and a nos terminator into the FseI site. As a result, pSB1852 was prepared. At last, the Δ15 RNAi cassette was inserted into the AscI site of the pSB1852 to prepare pSPB1877.

Figure 3:
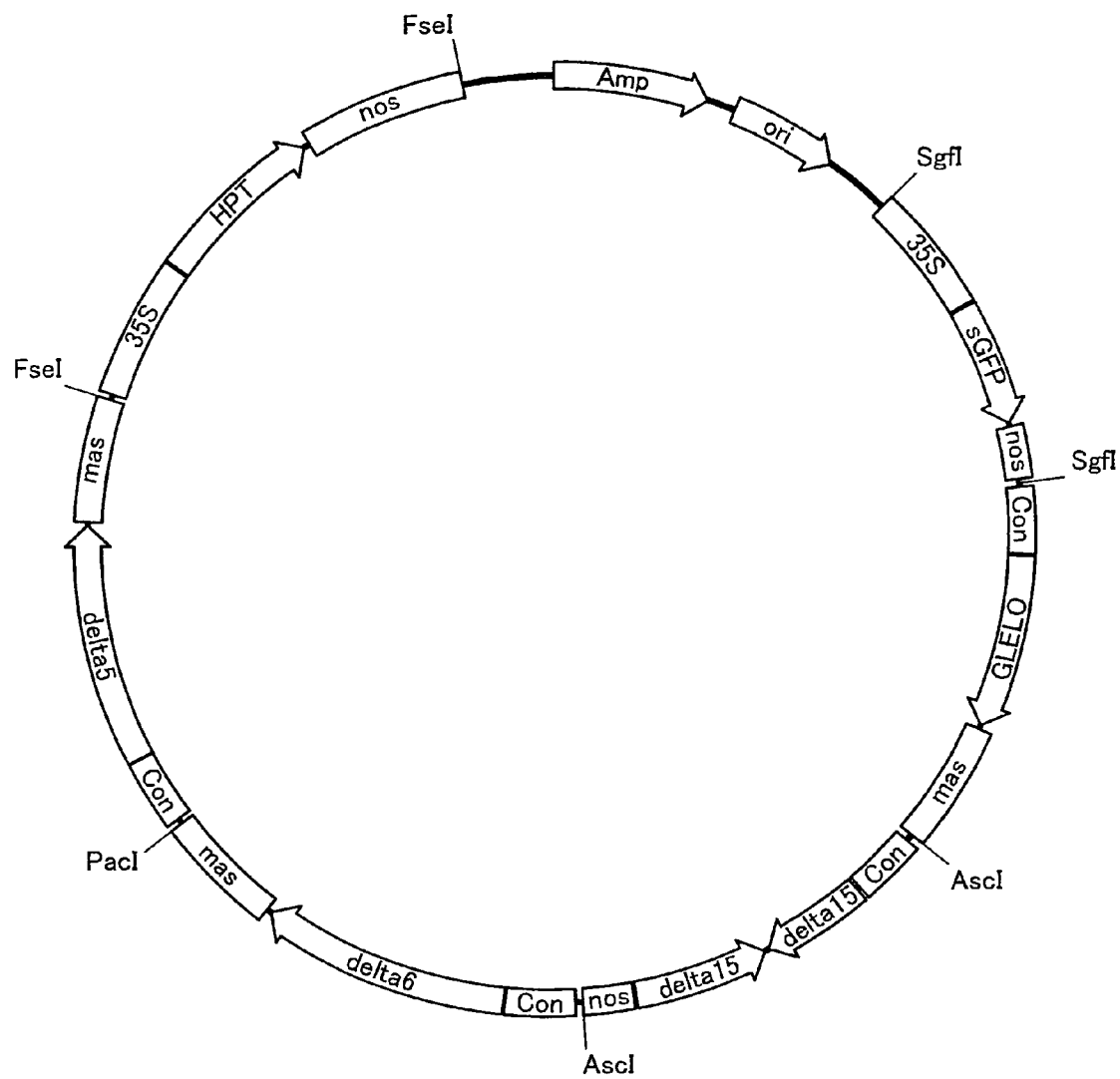
FIG. 3 is a diagram schematically illustrating an overall picture of the plasmid vector pSPB1877 according to the present invention.

FIG. 3 shows an overall view of pSB1877 prepared in such a manner. As illustrated, the pSB1877 is a multigene expression vector in which the GFP cassette, GLELO, Δ15 RNAi cassette, Δ6 desaturase, Δ5 desaturase, and HPT cassette are joined to one another.

[VI] Analysis of Transformation and Expression in Soybeans

Adventitious embryos that have incorporated the pSB1877 were sampled in their immature and mature stages to analyze the intake and expression of the multiple genes, as described below in detail.

Genomic DNA and RNA were prepared using a DNeasy Plant Mini Kit and a RNeasy Plant Mini Kit (Qiagen), respectively. A PCR reaction was carried out using 200 ng of extracted DNA as a template. As the primers, the following primers were used: det6f3 (5'-TGGTGGAAGGACAAGCA-CAA-3') (SEQ ID NO: 17); det6r2 (5'-ACAGACCAGGGT-GAACATCA-3') (SEQ ID NO: 18); det5f4 (5'-CTTTG-GATCCTTGATCGCCT-3') (SEQ ID NO: 19); det5r3 (5'-AGAACATGACGGTGTGCCAA-3') (SEQ ID NO: 20); XbaGLf (5'-CAGTTCTAGAGCCTTCTCACATTCCC-3') (SEQ ID NO: 21); SacGLr (5'-AGTCGAGCTCTTACTG-CAACTTCCTT-3') (SEQ ID NO: 22); HPTf1 (5'-CCT-GCGGGTAAATAGCTGCG-3') (SEQ ID NO: 23); HPTr1 (5'-CGTCAACCAAGCTCTGATAG-3') (SEQ ID NO: 24); EGFP-F1 (5'-ATGGTGAGCAAGGGCGAGGA-3') (SEQ ID NO: 25); and EGFP-R1 (5'-AATGAACATGTCGAG-CAGGTA-3') (SEQ ID NO: 26).

The PCR reaction used ExTaq (Takara Bio Inc.) as an enzyme, and was carried out by maintaining the sample at 94° C. for two minutes, and then by performing the reaction in 30 cycles at 94° C. for 30 seconds, at 55° C. for 30 seconds, and at 72° C. for 30 seconds to 1 minute, and finally maintaining the sample at 72° C. for one minute. The result revealed that the Δ6 desaturase, Δ5 desaturase, fatty-acid-chain elongase, and HPT gene were incorporated in the pSPB1877-introduced soybeans, but the GFP gene was not. Using the extracted total RNA, RT-PCR was carried out in the manner as described above. The RT-PCR was carried out with the transcript of the reverse transcription as a template, using primers det6f3 (SEQ ID NO: 17) and det6r2 (SEQ ID NO: 18), primers det5f4 and det5r3, and primers GLEf (5'-GT-GCTCGCTTATTTGGTCAC-3') (SEQ ID NO: 27) and GLEr (5'-CGACATCATGCAGAACTGTG-3') (SEQ ID NO: 28). PCR was carried out in the same cycle as that for the genomic DNA, and gene expression was analyzed. As a result of analysis, it was confirmed that the Δ6 desaturase, Δ5 desaturase, and fatty-acid-chain elongase were all expressed in the pSPB1877-transformed soybeans.

[VII] Lipids Analysis of Transformed Soybeans

According to the method described in the section [I] above, lipids were extracted from 1 g of mature embryo of the pSPB1877-transformed soybean, and their fatty acids were analyzed by gas chromatography and a mass spectrometer. The analysis result is shown in Table 2.

TABLE 2

|  | Control (%) | pSPB1877 (%) |
|---|---|---|
| linoleic acid | 56.28 | 43.96 |
| α-linolenic acid | 7.6 | 6.52 |
| γ-linolenic acid | 0 | 2.77 |
| dihomo-γ-linolenic acid | 0 | 1.73 |
| arachidonic acid | 0 | 2.1 |

As shown in Table 2, the mature embryo of the pSPB1877-transformed soybean synthesized γ-linolenic acid, dihomo-γ-linolenic acid, and arachidonic acid, which are not produced in the soybeans in nature. The proportions of these fatty acids in a total fatty acids were 2.77%, 1.73%, and 2.10%, respectively. Note that, γ-linolenic acid, dihomo-γ-linolenic acid, and arachidonic acid were not contained in the lipids of the wild-type soybeans.

The result proves that a plant producing process according to the present invention can produce arachidonic acid in soybeans.

VIII

According to the method described in the section [I] above, lipids were extracted from one of the seeds of the pSPB1877-transformed soybean, and the fatty acids contained were analyzed by gas chromatography and a mass spectrometer. The analysis result is shown in Table 3.

TABLE 3

|  | Control Seed (%) | pSPB1877 Seed (%) |
|---|---|---|
| linoleic acid | 57.86 | 51.19 |
| α-linolenic acid | 9.27 | 1.92 |
| γ-linolenic acid | 0 | 2.49 |
| dihomo-γ-linolenic acid | 0 | 1.05 |
| arachidonic acid | 0 | 0.83 |

As shown in Table 3, the seed of the pSPB1877-transformed soybean synthesized γ-linolenic acid, dihomo-γ-linolenic acid, and arachidonic acid, which are not produced in wild-type soybeans. The proportions of these fatty acids in total fatty acids were 2.49%, 1.05%, and 0.83%, respectively. In addition, the expression level of α-linolenic acid in the transformant showed about 20% decrease from that of the wild-type soybean. This suggests the possibility of the RNAi suppressing the expression of Δ15 desaturase.

As these results indicate, the change in the lipid composition of the transformant's seed proves the inheritance of the modified fatty acid trait to the next generation. Therefore, cultivation of the recombinant soybean enables mass production of soybean seeds having modified fatty acid compositions.

IX

T1 seeds of the pSPB1877-transformed soybean accumulating arachidonic acid were sown to produce next generation T2 seeds. Using DNA extracted from T1 plant leaves as a template, genomic PCR was carried out for the Δ6 desaturase, chain elongase, and Δ5 desaturase according to the method described in the section [VI] above. The result confirmed that the T1 plant inherited the three genes of these enzymes. Further, DNA was prepared from the T1 plant leaves by Nucleon Phytopure (Amersham), and Southern blotting was carried out with Δ6 desaturase, chain elongase, and Δ5 desaturase probes prepared by using a DIG DNA labeling kit (Roche Diagnostics), and the primers described in the section [VI] above. The result confirmed that at least two copies of constructs were introduced into the T1 plant. The result of lipid analysis for the T2 seed revealed, as shown in Table 4, that the proportions of γ-linolenic acid, dihomo-γ-linolenic acid, and arachidonic acid, which are not produced in wild-type soybeans, were 1.71%, 0.55%, and 0.53%, respectively, with respect to total fatty acids. Further, by the RT-PCR of the T2 seed, expressions of the Δ6 desaturase, chain elongase, and Δ5 desaturase were confirmed. Therefore, it was confirmed that the transgenes were stably passed onto the next generation, and that the trait of modified lipid composition was also inherited to the next generation.

Further, as a result RT-PCR, no transcript was detected for the endogenous Δ15 desaturase (Accession No. L22964). This indicates that transcription of Δ15 desaturase was effectively suppressed by RNAi, as evidenced by the reduced α-linolenic acid level.

TABLE 4

|  | Control Seed (%) | pSPB1877-1 T2Seed (%) |
|---|---|---|
| linoleic acid | 57.86 | 53.27 |
| α-linolenic acid | 9.27 | 3.07 |
| γ-linolenic acid | 0 | 1.71 |
| dihomo-γ-linolenic acid | 0 | 0.55 |
| arachidonic acid | 0 | 0.53 |

INDUSTRIAL APPLICABILITY

As described above, a producing process of oil or fat source plants according to the present invention can produce plants containing arachidonic acid, which are not produced in nature by higher plants. The plants can be used to readily obtain a large amount of arachidonic acid, which can then be marketed for the manufacture or distribution of health food or medicines. That is, the present invention is applicable to the food industry, pharmaceutical industry, and all other industries related to these fields. Further, with the present invention, the value of plants can be increased, making the invention also applicable to agricultures.

The invention claimed is:

1. An arachidonic acid-containing plant comprising fatty acid synthetase genes associated with the biosynthesis of arachidonic acid, wherein the fatty acid synthetases associated with the biosynthesis of arachidonic acid are a Δ6 desaturase consisting of the amino acid sequence of SEQ ID NO: 1, a fatty-acid-chain elongase consisting of the amino acid sequence of SEQ ID NO: 3, and a Δ5 desaturase consisting of the amino acid sequence of SEQ ID NO: 5, and wherein the expression of a Δ15 desaturase is suppressed in the plant.

2. The arachidonic acid-containing plant as set forth in claim 1, wherein the gene encoding the Δ6 desaturase
has the nucleotide sequence of SEQ ID NO: 2 as an open reading frame.

3. The arachidonic acid-containing plant as set forth in claim 1, wherein the gene encoding the fatty-acid-chain elongase
has the nucleotide sequence of SEQ ID NO: 4 as an open reading frame.

4. The arachidonic acid-containing plant as set forth in claim 1, wherein the gene encoding the Δ5 desaturase
has the nucleotide sequence of SEQ ID NO: 6 as an open reading frame.

5. The arachidonic acid-containing plant as set forth in claim 1, wherein the genes encoding the fatty acid synthetases associated with the biosynthesis of arachidonic acid are derived from *Mortierella*.

6. The arachidonic acid-containing plant as set forth in claim 1, wherein the genes encoding the fatty acid synthetases associated with the biosynthesis of arachidonic acid are derived from *Mortierella alpina*.

7. The arachidonic acid-containing plant as set forth in claim 1, wherein the expression of the Δ15 desaturase is suppressed by an RNAi method.

8. The arachidonic acid-containing plant as set forth in claim 1, wherein the plant comprises a plant cell, a plant tissue, a plant callus, a plant seed, a grown plant individual, or offspring of the plant individual that contains arachidonic acid.

9. The arachidonic acid-containing plant as set forth in claim 1, wherein the plant comprises a soybean.

10. An arachidonic acid-containing plant preparation kit for preparing the arachidonic acid-containing plant of claim 1, comprising:
a recombinant expression vector including a promoter and genes encoding a Δ6 desaturase consisting of the amino acid sequence of SEQ ID NO: 1, a fatty-acid-chain elongase consisting of the amino acid sequence of SEQ ID NO: 3, and a Δ5 desaturase consisting of the amino acid sequence of SEQ ID NO: 5.

11. The arachidonic acid-containing plant preparation kit as set forth in claim 10, further comprising a set of reagents for introducing the recombinant expression vector into a plant cell.

* * * * *

SEQUENCE LISTING

```
<160> NUMBER OF SEQ ID NOS: 28

<210> SEQ ID NO 1
<211> LENGTH: 457
<212> TYPE: PRT
<213> ORGANISM: Mortierella alpina

<400> SEQUENCE: 1

Met Ala Ala Ala Pro Ser Val Arg Thr Phe Thr Arg Ala Glu Ile Leu
  1               5                  10                  15

Asn Ala Glu Ala Leu Asn Glu Gly Lys Lys Asp Ala Glu Ala Pro Phe
             20                  25                  30

Leu Met Ile Ile Asp Asn Lys Val Tyr Asp Val Arg Glu Phe Val Pro
         35                  40                  45

Asp His Pro Gly Gly Ser Val Ile Leu Thr His Val Gly Lys Asp Gly
     50                  55                  60

Thr Asp Val Phe Asp Thr Phe His Pro Glu Ala Ala Trp Glu Thr Leu
 65                  70                  75                  80

Ala Asn Phe Tyr Val Gly Asp Ile Asp Glu Ser Asp Arg Ala Ile Lys
                 85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Phe Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205
```

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Met Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Ile Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Gly Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Ala Ser Lys Met Gly Lys Ala Gln
    450                 455

<210> SEQ ID NO 2
<211> LENGTH: 1371
<212> TYPE: DNA
<213> ORGANISM: Mortierella alpina

<400> SEQUENCE: 2
atggctgctg ctcccagtgt gaggacgttt actcgggccg agattttgaa tgccgaggcc    60
ctgaatgagg gcaagaagga tgccgaggca ccctttctga tgatcattga caacaaggtg   120
tacgatgtcc gcgagtttgt ccctgatcat cccggtggaa gtgtgattct cacgcacgtt   180
ggcaaggacg gcactgacgt ctttgacact ttccaccccg aggctgcttg ggagactctt   240
gccaactttt acgttggtga tattgatgag agcgatcgtg ccatcaagaa tgatgacttt   300
gcggccgagg ttcgcaagct gcgcaccttg ttccagtccc ttggctacta cgactcgtcc   360
aaggcatact atgccttcaa ggtctcgttc aacctctgca tctggggctt gtcgactttc   420
attgttgcca gtggggccga gacctcgacc ctcgccaacg tgctctcggc tgcgctcttg   480
ggtctcttct ggcagcagtg cggatggttg gcgcacgact ttttgcacca ccaggtcttc   540
caggaccgtt tctggggtga cttttcggc gccttcttgg gaggtgtctg ccagggtttc   600
tcgtcctcct ggtggaagga caagcacaac actcaccacg ctgctcccaa cgtccacggc   660
gaggatcccg acattgacac tcaccctctg ttgacctgga gtgagcatgc tctggagatg   720

```
ttctcggatg ttcctgacga ggagctgacc cgtatgtggt cgcgcttcat ggtcctcaac    780
cagacctggt tctacttccc cattctctcg tttgcccgtc tgtcctggtg cctccagtcc    840
attatgtttg ttctgcccaa cggtcaggcc cacaagccct ctggagcgcg tgtgcccatt    900
tcgttggtcg agcagctgtc tctggctatg cactggacct ggtacctcgc caccatgttc    960
ctgttcatta aggatcccgt caacatgatt gtgtactttt tggtgtcgca ggctgtttgc   1020
ggcaacttgt tggcgattgt gttctcgctc aaccacaacg gcatgcctgt gatctccaag   1080
gaggaagcgg tcgatatgga cttcttcacc aagcagatca tcacgggtcg tgatgttcac   1140
cctggtctgt ttgccaactg gttcacgggt ggattgaact accagattga gcaccacttg   1200
ttcccttcga tgccccgcca caacttttca aagatccagc ctgctgtcga gactttgtgc   1260
aaaaagtacg gtgtccgata ccataccact ggtatgatcg agggaactgc agaggtcttt   1320
agccgtttga acgaggtctc caaggcggcc tccaagatgg gcaaggcaca g           1371
```

```
<210> SEQ ID NO 3
<211> LENGTH: 318
<212> TYPE: PRT
<213> ORGANISM: Mortierella alpina

<400> SEQUENCE: 3

Met Glu Ser Ile Ala Gln Phe Leu Pro Ser Lys Met Pro Gln Asp Leu
 1               5                  10                  15

Phe Ile Asp Leu Ala Arg Ala Ile Gly Val Gln Ala Ala Pro Tyr Val
                20                  25                  30

Asp Pro Leu Glu Ala Ala Leu Val Ala Gln Ala Glu Lys Phe Phe Pro
            35                  40                  45

Thr Val Val His His Thr Arg Gly Phe Leu Val Ala Val Glu Ser Pro
        50                  55                  60

Leu Ala Arg Glu Leu Pro Leu Met Asn Pro Phe His Val Leu Leu Ile
65                  70                  75                  80

Ala Leu Ala Tyr Leu Val Thr Val Phe Val Gly Met Gln Ile Met Lys
                85                  90                  95

Asn Phe Glu Arg Phe Glu Val Lys Thr Phe Ser Leu Phe His Asn Phe
                100                 105                 110

Cys Leu Val Ser Ile Ser Ala Tyr Met Cys Gly Gly Ile Leu Tyr Glu
            115                 120                 125

Ala Tyr Gln Ala Asn Tyr Gly Leu Phe Glu Asn Ala Ala Asp His Thr
        130                 135                 140

Val Gln Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Ile Gln
                245                 250                 255

Ser Ser Trp Asp Met Tyr Ala Met Lys Val Leu Gly Arg Pro Gly Tyr
```

```
              260             265             270
Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
        290                 295                 300

Ala Lys Ile Asp Ala Ala Lys Glu Lys Ala Arg Lys Leu Gln
305                 310                 315
```

```
<210> SEQ ID NO 4
<211> LENGTH: 954
<212> TYPE: DNA
<213> ORGANISM: Mortierella alpina

<400> SEQUENCE: 4
atggagtcga ttgcgcaatt cctcccctca aagatgccgc aagatctgtt tattgacctt      60
gcaagggcca tcggtgtcca ggccgcaccc tatgtcgacc ctctcgaggc agcgcttgtg     120
gcccaggccg agaagttctt ccccacggtc gttcatcaca cgcgcggctt tttggtcgcg     180
gtcgagtcac ccttggcccg tgagctgccc ttgatgaacc ccttccacgt gctgttgatc     240
gcgctcgctt acttggtcac ggtctttgtg ggcatgcaga tcatgaagaa ctttgaacgg     300
ttcgaggtca agacgttctc gctcttccac aacttttgtc tggtctcgat cagtgcctac     360
atgtgcggcg ggatcttgta cgaggcttac caggccaact atggactgtt tgagaacgcg     420
gccgatcata ccgtccaggg tcttcctatg ccaagatga tctggctctt ctacttctcc      480
aagatcatgg agtttgtcga caccatgatc atggtcctta agaagaacaa ccgccagatc     540
tcgttcttgc acgtctacca ccacagctcc atcttcacca tctggtggtt ggtcaccttt     600
gttgcaccca atggtgaagc ctacttctcg gctgcgttga actcgttcat ccacgtgatc     660
atgtacggct actacttcct gtccgccttg gcttcaagc aggtgtcgtt catcaagttc       720
tacatcacgc gttcgcagat gacgcagttc tgcatgatgt cgatccagtc ctcctgggac     780
atgtatgcca tgaaggtgct tggccgcccc ggatacccct tcttcatcac cgccctgctt     840
tggttctaca tgtggaccat gctcggactc ttctacaact tctacagaaa gaacgccaag     900
ttggccaagc aggccaagat cgatgctgcc aaggagaagg caaggaagtt gcag            954
```

```
<210> SEQ ID NO 5
<211> LENGTH: 446
<212> TYPE: PRT
<213> ORGANISM: Mortierella alpina

<400> SEQUENCE: 5

Met Gly Thr Asp Gln Gly Lys Thr Phe Thr Trp Gln Glu Leu Ala Ala
 1               5                  10                  15

His Asn Thr Glu Asp Ser Leu Leu Leu Ala Ile Arg Gly Asn Val Tyr
            20                  25                  30

Asp Val Thr Lys Phe Leu Ser Arg His Pro Gly Gly Thr Asp Thr Leu
        35                  40                  45

Leu Leu Gly Ala Gly Arg Asp Val Thr Pro Val Phe Glu Met Tyr His
    50                  55                  60

Glu Phe Gly Ala Ala Glu Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95

Lys Thr Ile Lys Gly Arg Val Glu Ala Tyr Phe Lys Asp Arg Asn Met
            100                 105                 110
```

Asp Ser Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
    210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
        275                 280                 285

Thr Val Met Phe Trp Gly Gly Lys Ala Phe Phe Val Trp Tyr Arg Leu
    290                 295                 300

Ile Val Pro Met Gln Tyr Leu Pro Leu Ser Lys Val Leu Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
        355                 360                 365

Asp Tyr Ala His Asp Ser His Leu Trp Thr Ser Ile Thr Gly Ser Leu
    370                 375                 380

Asn Tyr Gln Ala Val His His Leu Phe Pro Asn Val Ser Gln His His
385                 390                 395                 400

Tyr Pro Asp Ile Leu Ala Ile Ile Lys Asp Thr Cys Ser Glu Tyr Lys
                405                 410                 415

Val Pro Tyr Leu Val Lys Asp Thr Phe Trp Gln Ala Phe Ala Ser His
            420                 425                 430

Leu Glu His Leu Arg Val Leu Gly Leu Arg Pro Lys Glu Glu
        435                 440                 445

<210> SEQ ID NO 6
<211> LENGTH: 1338
<212> TYPE: DNA
<213> ORGANISM: Mortierella alpina

<400> SEQUENCE: 6
atgggtacgg accaaggaaa aaccttcacc tggcaagaac tcgcggcgca taacaccgag       60
gacagcctcc ttttggctat ccgtggcaat gtatacgatg tcacaaagtt cttgagccgt      120
catcctggtg aacggatac tctcttgctc ggagctggcc gagatgtcac tccggttttt       180
gagatgtacc acgagtttgg agctgcagag gctatcatga agaagtacta tgttggcaca      240
ctggtctcaa atgagttgcc catcttccca gagccaacgg tgttccataa gaccatcaag      300

```
ggcagagttg aggcatactt taaggaccgg aacatggatt ccaagaacag accagagatc    360
tggggacgat atgctctcat ctttggatcc ttgatcgcct cttactacgc gcagctcttt    420
gtaccgttcg tggtcgaacg tacatggctc caggtggtgt ttgctatcat catgggattt    480
gcgtgcgcgc aagtcggatt gaaccctctt cacgatgcct cccactttc agtgacccac     540 aaccccaccg tttggaagat tctcggagcc acgcacgact ttttcaacgg agcatcgtat    600
ctcgtgtgga tgtaccaaca tatgctcggc catcatccct ataccaacat tgctggagct    660
gatcccgatg tgtcgacctc tgagcccgat gttcgtcgta tcaagcccaa ccaaaagtgg    720
ttcgtcaacc acatcaacca gcacatgttt gttccttcc tgtacggact gctggcgttc     780
aaggtgcgca tccaggacat caacatcttg tactttgtca agaccaatga cgccattcgt    840
gtcaacccca tctcgacttg gcacaccgtc atgttctggg gcggaaaggc cttcttgtc     900 tggtaccgct tgatcgttcc tatgcagtat ctgcccctga gcaaggtgtt gctcttgttt    960
accgtcgcag acatggtctc ttcttactgg ctggcgctga ccttccaggc gaaccacgtt   1020
gttgaggagg ttcagtggcc attgcctgat gagaatggaa tcatccaaaa ggattgggca   1080
gccatgcagg tcgagactac tcaggattac gcccacgatt cgcacctctg gaccagcatc   1140
acgggcagct tgaactacca agccgttcat catctgttcc gaacgtttc ccagcatcac    1200 taccctgata tcctggctat catcaaggac acctgcagcg agtacaaggt gccatacctc   1260
gtcaaggata cctttggca agcgtttgct tcacatttgg agcacttgcg tgtgcttggt    1320
cttcgtccca aggaagag                                                  1338

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Primer
      HinCprof

<400> SEQUENCE: 7
agtcaagctt aattcaaaca aaaacg                                           26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Primer
      XbaCpror

<400> SEQUENCE: 8
cagttctaga aaattcttta atacgg                                           26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Primer
      Sacmasf

<400> SEQUENCE: 9
agtcgagctc cagcttccct gaaacc                                           26

<210> SEQ ID NO 10
<211> LENGTH: 33
<212> TYPE: DNA
```

```
<213> ORGANISM: Artificial Sequence
<220> FEATURE:
<223> OTHER INFORMATION: Description of Artificial Sequence: Primer
      Ecomasr

<400> SEQUENCE: 10
catcatctcg agggtggtga ccatggtgat cgc                              33

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Primer
      det15-2-f1

<400> SEQUENCE: 11
atggttaaag acacaaagcc tttagcc                                     27

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer
      det15-2-r1

<400> SEQUENCE: 12
tcagtctcgt tgcgagtgga gg                                          22

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Primer
      SOYF1-B

<400> SEQUENCE: 13
tggcctggga tccttaaaga cacaaagcct tta                              33

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Primer
      SOYR1-X

<400> SEQUENCE: 14
gcacatctcg agggattgaa gtgagagcct tc                               32

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Primer
      SOYF2-S

<400> SEQUENCE: 15
gtctgcgagc tcttaaagac acaaagcctt ta                               32

<210> SEQ ID NO 16
<211> LENGTH: 32
<212> TYPE: DNA
<213> ORGANISM: Artificial Sequence
<220> FEATURE:
```

```
<223> OTHER INFORMATION: Description of Artificial Sequence: Primer
      SOUR2-X

<400> SEQUENCE: 16
catcatctcg agggtggtga ccatggtgat gc                              32

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer
      det6f3

<400> SEQUENCE: 17
tggtggaagg acaagcacaa                                            20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer
      det6r2

<400> SEQUENCE: 18
acagaccagg gtgaacatca                                            20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer
      det5f4

<400> SEQUENCE: 19
ctttggatcc ttgatcgcct                                            20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer
      det5r3

<400> SEQUENCE: 20
agaacatgac ggtgtgccaa                                            20

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Primer
      XbaGLf

<400> SEQUENCE: 21
cagttctaga gccttctcac attccc                                     26

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Primer
      SacGLr
```

<400> SEQUENCE: 22
agtcgagctc ttactgcaac ttcctt                                          26

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Primer
      HPTf1

<400> SEQUENCE: 23
cctgcgggta aatagctgcg                                                 20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Primer
      HPTr1

<400> SEQUENCE: 24
cgtcaaccaa gctctgatag                                                 20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Primer
      EGFP-f1

<400> SEQUENCE: 25
atggtgagca agggcgagga                                                 20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Primer
      EGFP-R1

<400> SEQUENCE: 26
aatgaacatg tcgagcaggt a                                               21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Primer GLEf

<400> SEQUENCE: 27
gtgctcgctt atttggtcac                                                 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Primer GLEr

<400> SEQUENCE: 28
cgacatcatg cagaactgtg                                                 20